United States Patent
Whitacre et al.

(10) Patent No.: US 12,072,343 B2
(45) Date of Patent: Aug. 27, 2024

(54) REAGENT MIXING SYSTEM AND METHODS

(71) Applicant: Illumina, Inc., San Diego, CA (US)

(72) Inventors: Johanna L. Whitacre, San Diego, CA (US); Steven S. Phelps, San Diego, CA (US); Bradley Kent Drews, Poway, CA (US); Debra Sue Bryan, II, San Diego, CA (US); Michael A. Niziolek, San Diego, CA (US); Joshua A. Darland, Pleasanton, CA (US); Umberto Ulmanella, San Diego, CA (US); Michael Dai Wang, San Diego, CA (US); Michelle L. Alvarez, Encinitas, CA (US); Stephen Wayne Clark, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1000 days.

(21) Appl. No.: 17/062,288

(22) Filed: Oct. 2, 2020

(65) Prior Publication Data
US 2021/0018527 A1    Jan. 21, 2021

Related U.S. Application Data

(62) Division of application No. 15/846,885, filed on Dec. 19, 2017, now Pat. No. 10,830,784.
(Continued)

(30) Foreign Application Priority Data

Mar. 24, 2017  (GB) .................................. 1704747

(51) Int. Cl.
*G01N 35/10*   (2006.01)
*B01F 23/40*   (2022.01)
(Continued)

(52) U.S. Cl.
CPC ......... *G01N 35/1016* (2013.01); *B01F 23/45* (2022.01); *B01F 23/49* (2022.01);
(Continued)

(58) Field of Classification Search
None
See application file for complete search history.

(56) References Cited

U.S. PATENT DOCUMENTS 3,531,258 A    9/1970  Merrifield et al.
3,635,680 A *  1/1972  Peoples .................. G01N 35/08
                                                435/7.25
(Continued)

FOREIGN PATENT DOCUMENTS

CN        1309769 A      8/2001
CN      102740978 A     10/2012
(Continued)

OTHER PUBLICATIONS

PCT/US2017/067298, "International Search Report and Written Opinion" mailed Apr. 12, 2018, 25 pages.
(Continued)

*Primary Examiner* — Matthew D Krcha
(74) *Attorney, Agent, or Firm* — Dierker & Kavanaugh, P.C.

(57) ABSTRACT

A method includes, under control of control circuitry implementing a mixing protocol, aspirating reagents from multiple different reagent reservoirs into a cache channel. Designated amounts of the reagents are automatically aspirated from the corresponding reagent reservoirs by corresponding sippers based on the mixing protocol implemented by the control circuitry. The method also includes discharging the reagents from the cache channel into a mixing reservoir, and mixing the reagents within the mixing reservoir to form a reagent mixture.

7 Claims, 9 Drawing Sheets

Related U.S. Application Data

(60) Provisional application No. 62/442,647, filed on Jan. 5, 2017.

(51) Int. Cl.
| | | |
|---|---|---|
| *B01F 23/45* | (2022.01) | |
| *B01F 25/10* | (2022.01) | |
| *B01F 25/433* | (2022.01) | |
| *B01F 31/65* | (2022.01) | |
| *B01F 33/84* | (2022.01) | |
| *B01F 35/53* | (2022.01) | |
| *B01F 35/71* | (2022.01) | |
| *B01F 35/75* | (2022.01) | |
| *B01L 3/00* | (2006.01) | |
| *B01L 3/02* | (2006.01) | |
| *C12Q 1/6874* | (2018.01) | |
| *G01N 35/00* | (2006.01) | |
| *B01F 101/23* | (2022.01) | |

(52) U.S. Cl.
CPC ........ *B01F 25/103* (2022.01); *B01F 25/4331* (2022.01); *B01F 31/651* (2022.01); *B01F 33/84* (2022.01); *B01F 35/53* (2022.01); *B01F 35/7176* (2022.01); *B01F 35/7544* (2022.01); *B01L 3/0293* (2013.01); *B01L 3/502* (2013.01); *B01L 3/527* (2013.01); *C12Q 1/6874* (2013.01); *G01N 35/00584* (2013.01); *G01N 35/1002* (2013.01); *G01N 35/1097* (2013.01); *B01F 2101/23* (2022.01); *B01L 2200/0621* (2013.01); *B01L 2200/16* (2013.01); *B01L 2300/06* (2013.01); *B01L 2300/0867* (2013.01); *B01L 2300/0883* (2013.01); *B01L 2400/0487* (2013.01); *B01L 2400/0622* (2013.01); *B01L 2400/0633* (2013.01); *B01L 2400/086* (2013.01); *G01N 2035/1058* (2013.01)

(56) References Cited

U.S. PATENT DOCUMENTS

| | | |
|---|---|---|
| 7,105,354 B1 | 9/2006 | Shimoide |
| 7,150,999 B1 | 12/2006 | Shuck |
| 2002/0133002 A1* | 9/2002 | Heath ..................... G01N 1/40 536/25.4 |
| 2004/0181184 A1 | 9/2004 | Ericson et al. |
| 2006/0148063 A1 | 7/2006 | Fauzzi et al. |
| 2007/0128610 A1* | 6/2007 | Buzby ................ G01N 21/6458 435/6.16 |
| 2008/0095705 A1* | 4/2008 | Virtanen ............. B01F 33/3011 424/9.1 |
| 2009/0145202 A1 | 6/2009 | Tokhtuev et al. |
| 2009/0162840 A1 | 6/2009 | Fredriksson et al. |
| 2009/0249949 A1 | 10/2009 | Kepler et al. |
| 2010/0093069 A1 | 4/2010 | Squirrell |
| 2010/0111768 A1 | 5/2010 | Banerjee et al. |
| 2010/0300559 A1* | 12/2010 | Schultz .................... B01L 3/52 137/561 A |
| 2011/0052446 A1 | 3/2011 | Hirano et al. |
| 2011/0201121 A1* | 8/2011 | Kaartinen ............ B01L 3/0293 422/68.1 |
| 2013/0017621 A1 | 1/2013 | Kaminski et al. |
| 2013/0236375 A1 | 9/2013 | Tan et al. |
| 2013/0316336 A1 | 11/2013 | Matsui et al. |
| 2016/0319350 A1 | 11/2016 | Stone et al. |

FOREIGN PATENT DOCUMENTS

| | | |
|---|---|---|
| CN | 101970111 A | 9/2013 |
| CN | 103308360 A | 9/2013 |
| CN | 102906573 B | 2/2015 |
| CN | 105004596 A | 10/2015 |
| CN | 104487562 A | 9/2016 |
| EP | 0718619 | 6/1966 |
| EP | 0912885 | 5/1999 |
| EP | 2878954 | 6/2015 |
| FR | 2868337 | 5/2006 |
| JP | H01180229 | 12/1989 |
| JP | 2004154642 A | 6/2004 |
| JP | 2006090854 A | 4/2006 |
| JP | 2015514218 A | 5/2015 |
| WO | 2005094976 A1 | 10/2005 |
| WO | WO 2007023205 | 3/2007 |
| WO | 2013151622 A1 | 10/2013 |

OTHER PUBLICATIONS

UK Application No. 1704747.3 Search Report dated Sep. 20, 2017, 1 page.

* cited by examiner

REAGENT MIXING SYSTEM AND METHODS

CROSS-REFERENCE TO RELATED APPLICATIONS

This application is a divisional of U.S. application Ser. No. 15/846,885, filed Dec. 19, 2017, which itself claims the benefit of U.S. Provisional Application Ser. No. 62/442,647, filed Jan. 5, 2017, and claims priority to Great Britain (GB) Patent Application Number 1704747.3, filed Mar. 24, 2017, which itself claims priority to U.S. Provisional Application Ser. No. 62/442,647, filed Jan. 5, 2017, the contents of each of which is incorporated by reference herein in its entirety.

BACKGROUND

Instruments have been developed and continue to evolve for sequencing molecules of interest, particularly deoxyribonucleic acids (DNA), ribonucleic acids (RNA) and other biological samples. In advance of sequencing operations, samples of the molecules of interest are prepared in order to form a library or template which will be mixed with reagents and ultimately introduced into a flow cell where individual molecules will attach at sites and be amplified to enhance detectability. The sequencing operation, then, includes repeating a cycle of steps to bind the molecules at the sites, tag the bound components, image the components at the sites, and process the resulting image data.

In such sequencing systems, the reagents may be manually mixed with each other to create a reagent mix, and the reagent mix is then manually mixed with the sample template and loaded into a cluster station to be flowed over the flow cell. The performance of the sequencing operation may be affected by various reagent factors, such as the amounts of each of the reagents in the reagent mix, the order in which the reagents are mixed, how well the reagents are mixed together and with the sample template, the temperature of the reagent mix, the amount of time that accrues from the time that the reagents are mixed and the time that the combined reagent mix and sample template is loaded into the cluster station, and the like. The use of manual transfer and mixing of the reagents introduces variability in the reagent factors, which can be detrimental to the performance of the sequencing operation. For example, insufficient mixing of the reagents and sample template can result in reduced performance characterized by a lower yield of quality clusters of molecules on the flow cell that are used for sequencing.

INTRODUCTION

In an example, a method (e.g., for mixing reagents) is provided that includes, under control of control circuitry implementing a mixing protocol, aspirating reagents from multiple different reagent reservoirs into a cache channel. Designated amounts of the reagents are automatically aspirated from the corresponding reagent reservoirs by corresponding sippers based on the mixing protocol implemented by the control circuitry. The method also includes discharging the reagents from the cache channel into a mixing reservoir, and mixing the reagents within the mixing reservoir to form a reagent mixture.

In an example, the method further comprises delivering the reagent mixture to a flow cell, the reagent mixture reacting with a sample template on the flow cell to produce clonal populations of deoxyribonucleic acid (DNA) molecules on the flow cell.

In an example of the method, the mixing reservoir contains a sample template therein prior to discharging the reagents from the cache channel into the mixing reservoir.

In a further example, the reagents in the mixing reservoir are mixed by aspirating a volume of the reagent mixture into a nozzle sipper extending into the mixing reservoir and subsequently discharging the volume of the reagent mixture from the nozzle sipper back into the mixing reservoir. In this example, the nozzle sipper contains a buffer fluid therein, and the method further comprises introducing air into the nozzle sipper prior to aspirating the volume of the reagent mixture into the nozzle sipper to define an air gap between the buffer fluid and the reagent mixture that is aspirated into the nozzle sipper to avoid mixing between the buffer fluid and the reagent mixture.

In an example of the method, the reagents are aspirated into the cache channel one at a time in an ordered sequence. In this example, the cache channel includes an alternating pattern of the designated amounts of the different reagents along a length of the cache channel in response to aspirating the reagents into the cache channel.

In another example of the method, the reagents are aspirated into the cache channel from the different reagent reservoirs one at a time in an ordered sequence that is repeated at least once before the reagents in the cache channel are discharged into the mixing reservoir.

In an example, a first volume of the reagents is aspirated into the cache channel and a second, smaller volume of the reagents is discharged into the mixing reservoir such that a residual volume of the reagents defining an upstream buffer zone remains in the cache channel after discharging the reagents into the mixing reservoir.

In an example of the method, the reagents are aspirated from the corresponding reagent reservoirs using sippers that extend into the corresponding reagent reservoirs, the sippers fluidly being connected to the cache channel through corresponding ports and fluid channels on a fluid manifold.

An example of the method further comprises introducing a surfactant into the reagents to reduce a difference in miscibility between the reagents.

In an example, at least some of the reagents have different specific gravities relative to each other.

Another example of the method further comprises introducing a crowding agent having a molecular weight less than 10,000 Daltons into the reagents to reduce viscosity of the reagents.

It is to be understood that any features of the method may be combined together in any desirable manner and/or configuration.

In another example, a system (e.g., for mixing reagents) is provided that includes multiple sippers, a cache channel, and control circuitry. The multiple sippers include a nozzle sipper and multiple reagent sippers. The reagent sippers extend into different corresponding reagent reservoirs containing different reagents therein such that respective distal tips of the reagent sippers contact the reagents in the reagent reservoirs. The nozzle sipper extends into a mixing reservoir. The cache channel extends between a pump end and a reservoir end. The pump end of the cache channel is operatively connected to a pump. The reservoir end of the cache channel is fluidly connected to the sippers through a reagent selector valve and corresponding fluid channels. The control circuitry is operatively connected to the pump and the reagent selector valve. The control circuitry implements a mixing protocol by controlling the pump and the reagent selector valve to automatically aspirate the reagents through the corresponding reagent sippers into the cache channel at designated amounts of the corresponding reagents based on the mixing protocol. The control circuitry subsequently controls the pump and the reagent selector valve to discharge the reagents from the cache channel through the nozzle sipper into the mixing reservoir and mix the reagents within the mixing reservoir to form a reagent mixture.

In an example of the system, the control circuitry controls the pump to mix the reagents within the mixing reservoir by aspirating a volume of the reagent mixture into the nozzle sipper and subsequently discharging the volume of the reagent mixture from the nozzle sipper back into the mixing reservoir. In this example, the control circuitry controls the pump and the reagent selector valve to aspirate and subsequently discharge the reagent mixture within the mixing reservoir multiple times to mix the reagents. In this example, wherein the nozzle sipper contains a buffer fluid therein, the control circuitry controlling the pump to introduce air into the nozzle sipper prior to aspirating the reagent mixture into the nozzle sipper to define an air gap between the buffer fluid and the reagent mixture that is aspirated into the nozzle sipper to avoid mixing the buffer fluid and the reagent mixture.

In an example of the system, an inner diameter of the nozzle sipper is smaller than respective inner diameters of the reagent sippers.

In an example of the system, the control circuitry further controls the pump and the reagent selector valve to deliver the reagent mixture to a flow cell that is fluidly connected to the mixing reservoir through the nozzle sipper and the reagent selector valve, the reagent mixture reacting with a sample template on the flow cell to produce clonal populations of DNA molecules on the flow cell.

In an example of the system, the control circuitry controls the pump and the reagent selector valve to aspirate the different reagents into the cache channel one at a time in an ordered sequence and to repeat the ordered sequence at least once before the reagents in the cache channel are discharged into the mixing reservoir.

In another example of the system, the control circuitry controls the pump and the reagent selector valve to aspirate a first volume of the reagents into the cache channel and to subsequently discharge a second, smaller volume of the reagents from the cache channel into the mixing reservoir such that a residual volume of the reagents defining an upstream buffer zone remains in the cache channel after discharging the reagents into the mixing reservoir.

It is to be understood that any features of the system may be combined together in any desirable manner. Moreover, it is to be understood that any combination of features of the system and/or of the method may be used together, and/or that any features from either or both of these aspects may be combined with any of the examples disclosed herein.

In another example, a system (e.g., for mixing reagents) is provided that includes a fluid manifold, a reagent selector valve, and a pump. The fluid manifold includes multiple sippers and a cache channel. The sippers include multiple reagent sippers and a nozzle sipper. The reagent sippers extend into different corresponding reagent reservoirs containing different reagents therein such that distal tips of the reagent sippers contact the reagents. The nozzle sipper extends into a mixing reservoir. The cache channel extends between a pump end and a reservoir end. The reservoir end is fluidly connected to the sippers through corresponding fluid channels along the fluid manifold. The reagent selector valve is operatively connected between the cache channel and the sippers. The pump is operatively connected to the pump end of the cache channel. The pump and the reagent selector valve are automatically controlled according to a mixing protocol to aspirate the reagents from the reagent reservoirs through the corresponding reagent sippers into the cache channel at designated amounts of the corresponding reagents based on the mixing protocol. The pump and the reagent selector valve are automatically controlled to subsequently discharge the reagents from the cache channel through the nozzle sipper into the mixing reservoir and mix the reagents within the mixing reservoir to form a reagent mixture by aspirating a volume of the reagent mixture from the mixing reservoir into the nozzle sipper and subsequently discharging the volume of the reagent mixture out of the nozzle sipper back into the mixing reservoir.

In an example of this system, the pump and the reagent selector valve are automatically controlled to aspirate the reagents from the reagent reservoirs into the cache channel one at a time in an ordered sequence and to repeat the ordered sequence at least once before discharging the reagents from the cache channel into the mixing reservoir.

In an example of this system, the fluid manifold, the reagent selector valve, and the pump are commonly disposed within a housing of an instrument.

It is to be understood that any features of this example system may be combined together in any desirable manner. Moreover, it is to be understood that any combination of features of this example system and/or of the other example system and/or of the method may be used together, and/or that any features from either or any of these aspects may be combined with any of the examples disclosed herein.

In another example, an instrument (e.g., for mixing reagents) is provided that includes a housing, a fluid manifold, a pump, a reagent selector valve, and a flow cell. The fluid manifold is disposed within the housing and includes multiple channels fluidly connected to sippers that extend into different corresponding reservoirs. The pump is disposed within the housing and operatively connected to at least one of the channels of the fluid manifold. The reagent selector valve is disposed within the housing and operatively connected to at least two of the channels of the fluid manifold. The flow cell is disposed within the housing and fluidly connected to at least one of the channels of the fluid manifold. The pump and the reagent selector valve are automatically controlled according to a mixing protocol to transfer reagents that are contained within at least some of the reservoirs from the corresponding reservoirs through the sippers into the channels of the fluid manifold at designated amounts of the corresponding reagents based on the mixing protocol. The pump and the reagent selector valve are automatically controlled to mix the reagents that were transferred to the fluid manifold to form a reagent mixture and subsequently deliver the reagent mixture from the fluid manifold to the flow cell.

It is to be understood that any features of the instrument may be combined together in any desirable manner. Moreover, it is to be understood that any combination of features of the instrument and/or of the example systems and/or of the method may be used together, and/or that any features from either or any of these aspects may be combined with any of the examples disclosed herein.

BRIEF DESCRIPTIONS OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
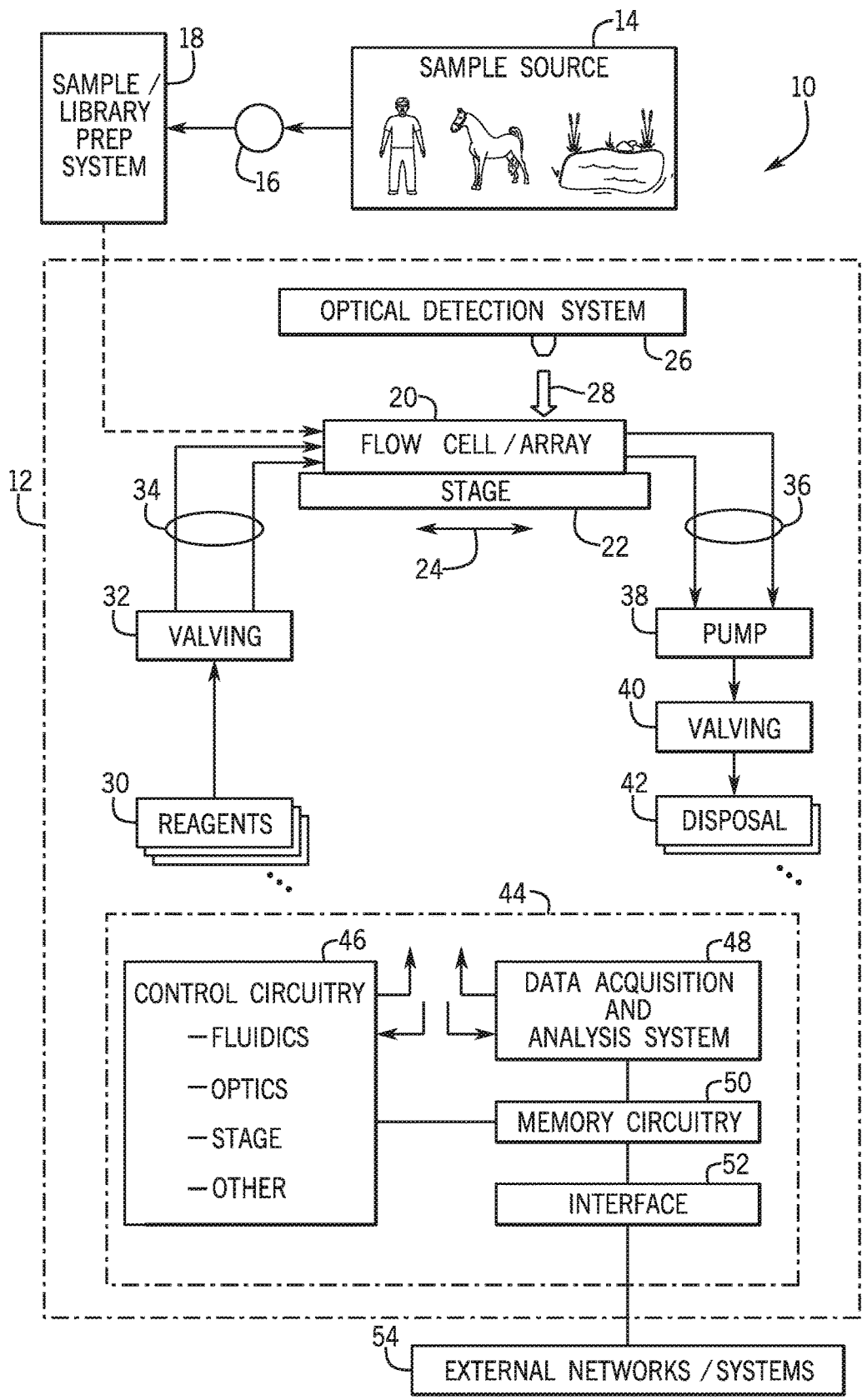
FIG. 1 is a diagrammatical overview of an example sequencing system in which the disclosed techniques may be employed.

FIG. 1 illustrates an example of a sequencing system 10 to process molecular samples that may be sequenced to determine their components, the component ordering, and generally the structure of the sample. The system 10 includes an instrument 12 that receives and processes a sample 16 including molecules of interest in a sequence that is sought to be determined. The sample 16 may include organic molecules from an organism or synthesized molecules created in a lab. The molecules of interest may include DNA, RNA, or other molecules having base pairs, the sequence of which may define genes and variants having particular functions of ultimate interest. The sample 16 is provided by or originates from a sample source 14. The sample source 14 may include, for example, an individual or subject, such as a human, animal, microorganism, plant, or other donor (including environmental samples).

The sample 16 is introduced into a sample/library preparation system 18. The system 18 prepares the sample 16 for analysis. Preparation may include isolating, breaking, and otherwise preparing the sample 16 for analysis. The resulting library includes the molecules of interest in lengths that facilitate the sequencing operation. The resulting library is then provided to the instrument 12 where the sequencing operation is performed. The library, which is referred to herein as a sample template, is combined with reagents in an automated or semi-automated process, and then introduced to the flow cell 20 prior to sequencing. In some examples the library may be pre-mixed with reagents before being routed to the flow cell, e.g., the library may be routed through a selector valve system, such as is described below, and mixed with reagents in a destination recipient before being transferred to the flow cell.

In the example illustrated in FIG. 1, the instrument 12 includes a flow cell 20 that receives the sample template. The flow cell 20 includes one or more fluidic channels or lanes that allow for sequencing chemistry to occur, including attachment of the molecules of the library, and amplification at locations or sites that can be detected during the sequencing operation. For example, the flow cell 20 may include sequencing templates immobilized on one or more surfaces at amplification locations or sites. The flow cell 20 may include a patterned array, such as a microarray, a nanoarray, and so forth, of amplification sites. In practice, the amplification sites may be disposed in a regular, repeating pattern, a complex non-repeating pattern, or in a random arrangement on one or more surfaces of a support. To enable the sequencing chemistry to occur, the flow cell 20 also allows for introduction of substances, such as various reagents, buffers, and other reaction media, that are used for reactions, flushing, and so forth. The substances flow through the flow cell 20 and may contact the molecules of interest at the individual amplification sites.

In the instrument 12, the flow cell 20 may be mounted on a movable stage 22 that, in an example, may be movable in one or more directions as indicated by reference numeral 24. The flow cell 20 may, for example, be provided in the form of a removable and replaceable cartridge that may interface with ports on the movable stage 22 or other components of the system 10 in order to allow reagents and other fluids to be delivered to or from the flow cell 20. The stage 22 is associated with an optical detection system 26 that can direct radiation or light 28 to the flow cell 20 during sequencing. The optical detection system 26 may employ various methods, such as fluorescence microscopy methods, for detection of the analytes disposed at the sites of the flow cell 20. By way of example, the optical detection system 26 may employ confocal line scanning to produce progressive pixilated image data that can be analyzed to locate individual sites in the flow cell 20 and to determine the type of nucleotide that was most recently attached or bound to each site. Other imaging techniques may also suitably be employed, such as techniques in which one or more points of radiation are scanned along the sample or techniques employing "step and shoot" imaging approaches. The optical detection system 26 and the stage 22 may cooperate to maintain the flow cell 20 and the detection system 26 in a static relationship while obtaining an area image, or, as noted, the flow cell 20 may be scanned in any suitable mode (e.g., point scanning, line scanning, "step-and-shoot" scanning).

While many different technologies may be used for imaging, or more generally for detecting the molecules at the sites, presently contemplated examples may make use of confocal optical imaging at wavelengths that cause excitation of fluorescent tags. The tags, excited by virtue of their absorption spectrum, return fluorescent signals by virtue of their emission spectrum. The optical detection system 26 is configured to capture such signals, to process pixelated image data at a resolution that allows for analysis of the signal-emitting sites, and to process and store the resulting image data (or data derived from it).

In a sequencing operation, cyclic operations or processes are implemented in an automated or semi-automated fashion in which reactions are promoted, such as with single nucleotides or with oligonucleotides, followed by flushing, imaging and de-blocking in preparation for a subsequent cycle. The sample template, prepared for sequencing and immobilized on the flow cell 20, may undergo a number of such cycles before all useful information is extracted from the sample template. The optical detection system 26 may generate image data from scans of the flow cell 20 (and its sites) during each cycle of the sequencing operation by use of electronic detection circuits (e.g., cameras or imaging electronic circuits or chips). The resulting image data may then be analyzed to locate individual sites in the image data, and to analyze and characterize the molecules present at the sites, such as by reference to a specific color or wavelength of light (a characteristic emission spectrum of a particular fluorescent tag) that was detected at a specific location, as indicated by a group or cluster of pixels in the image data at the location. In a DNA or RNA sequencing application, for example, the four common nucleotides may be represented by distinguishable fluorescence emission spectra (wavelengths or wavelength ranges of light). Each emission spectrum, then, may be assigned a value corresponding to that nucleotide. Based upon this analysis, and tracking the cyclical values determined for each site, individual nucleotides and their orders may be determined for each site. The sequences may then be further processed to assemble longer segments including genes, chromosomes, and so forth. As used in this disclosure, the terms "automated" and "semi-automated" mean that the operations are performed by system programming or configuration with little or no human interaction once the operations are initiated, or once processes including the operations are initiated.

In the illustrated example, reagents 30 are drawn or aspirated into the flow cell 20 through valving 32. The valving 32 may access the reagents 30 from reservoirs or vessels in which they are stored, such as through pipettes or sippers (not shown in FIG. 1). The valving 32 may allow for selection of the reagents 30 based upon a prescribed sequence of operations performed in a protocol that is stored in a memory. The valving 32 may further receive commands for directing the reagents 30 through flow paths 34 into the flow cell 20. Exit or effluent flow paths 36 direct the used reagents 30 from the flow cell 20. In the illustrated example, a pump 38 serves to move the reagents 30 through the system 10. The pump 38 may also serve other useful functions, such as measuring reagents 30 or other fluids through the system 10, aspirating air or other fluids, and so forth. Additional valving 40 downstream of the pump 38 allows for appropriately directing the used reagents 30 to disposal vessels or reservoirs 42.

The instrument 12 further includes a range of circuitry that aids in commanding the operation of the various system components, monitoring such operation by feedback from sensors, collecting image data, and at least partially processing the image data. In the example illustrated in FIG. 1, a control supervisory system 44 includes control circuitry 46, a data acquisition and analysis system 48, memory circuitry 50, and an interface 52. Both the control circuitry 46 and the data acquisition and analysis system 48 include one or more processors (e.g., the processors 100 shown in FIG. 3, examples of which include digital processing circuits, such as microprocessors, multi-core processors, FPGA's, or any other suitable processing circuitry) that are operatively connected to the memory circuitry 50 (e.g., solid state memory devices, dynamic memory devices, on and/or off-board memory devices, and so forth) that may store machine-executable instructions for controlling, for example, one or more computers, processors, or other similar logical devices to provide certain functionality. Application-specific or general purpose computers may at least partially make up the control circuitry 46 and the data acquisition and analysis system 48. The control circuitry 46 may include, for example, circuitry configured (e.g., programmed) to process commands for fluidics, optics, stage control, and any other useful functions of the instrument 12. The data acquisition and analysis system 48 interfaces with the optical detection system 26 to command movement of the optical detection system 26 and/or the stage 24, the emission of light for cyclic detection, the reception and processing of returned signals, and so forth. The instrument 12 may also include various interfaces 52 (e.g., interface devices), such as an operator interface that permits control and monitoring of the instrument 12, transfer of samples, launching of automated or semi-automated sequencing operations, generation of reports, and so forth. Finally, in the example of FIG. 1, external networks or systems 54 maybe coupled to and cooperate with the instrument 12 for analysis, control, monitoring, servicing, and/or other operations.

In one or more examples described herein, the instrument 12 is to provide onboard, automated transfer and mixing of the reagents 30 prior to flowing the combined reagent and sample template mixture onto the flow cell 20 for cluster generation. The instrument 12 controls various reagent factors, including the amounts of the reagents 30 that are mixed together, the order in which the reagents 30 are drawn from corresponding reagent reservoirs, temperature, and timing (e.g., duration that the reagents 30 are in a pre-mixed state before mixing with the sample template), with a greater precision and repeatability than can be achieved via manual transfer and mixing of the reagents 30. The instrument 12 additionally mixes the reagents 30 and the sample template such that the resulting mixture, referred to herein as a clustering mixture, is sufficiently homogenous to achieve a threshold quality and quantity of molecule clusters on the flow cell 20 for desired sequencing performance.

It may be noted that while a single flow cell 20 and fluidics path and a single optical detection system 26 are illustrated in FIG. 1, in some instruments 12 more than one flow cell 20 and fluidics path may be accommodated. For example, two or more such arrangements may be provided to enhance sequencing and throughput. In practice, any number of flow cells 20 and paths may be provided. These may make use of the same or different reagent receptacles, disposal receptacles, control systems, image analysis systems, and so forth. The multiple flow cells 20 and fluidics paths may be individually controlled or controlled in a coordinated fashion. It is to be understood that the phrase "fluidically connected" may be used herein to describe connections between two or more components that place such components in fluidic communication with one another, much in the same manner that "electrically connected" may be used to describe an electrical connection between two or more components. The phrase "fluidically interposed" may be used, for example, to describe a particular ordering of components. For example, if component B is fluidically interposed between components A and C, then fluid flowing from component A to component C would flow through component B before reaching component C.

Figure 2:
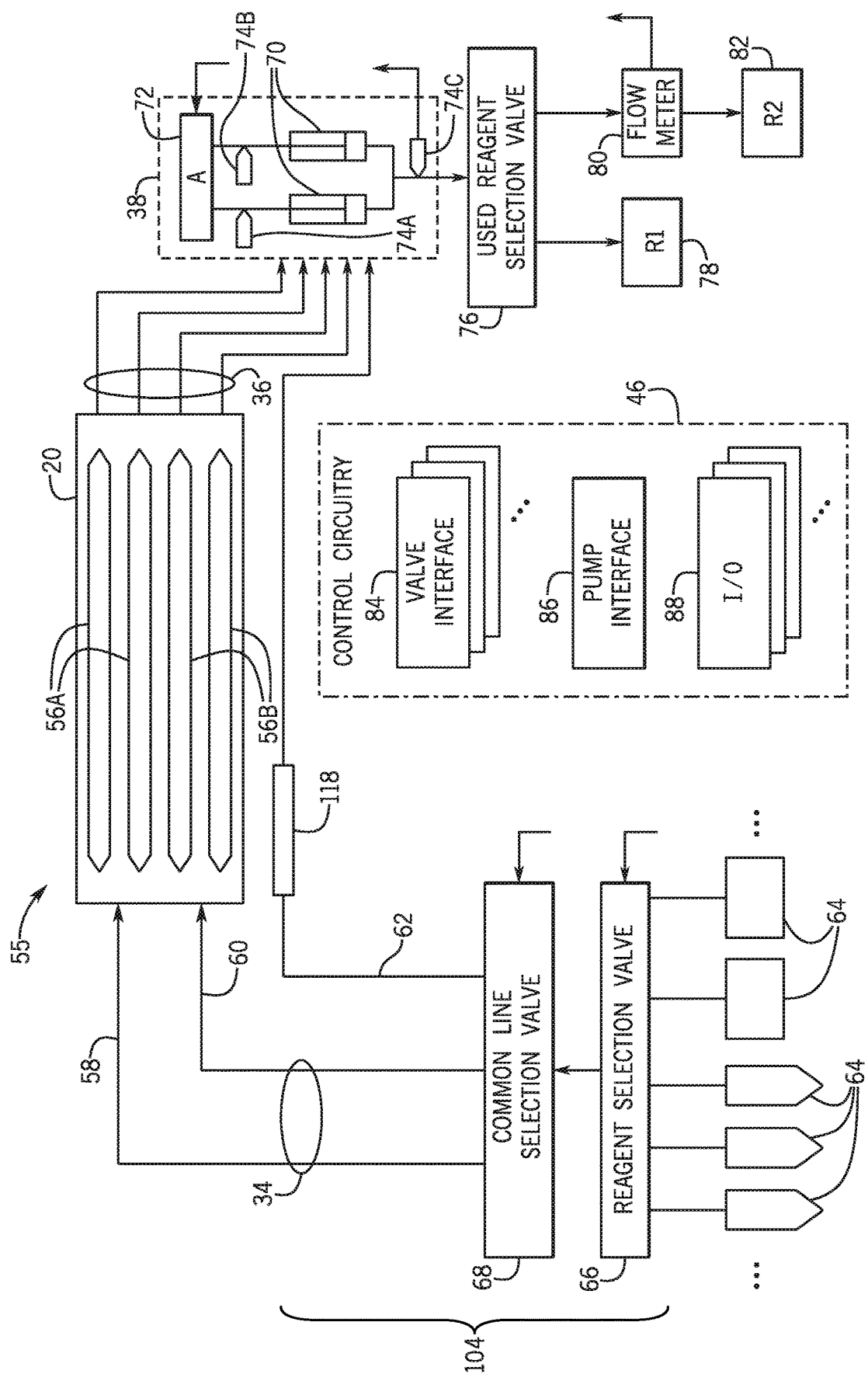
FIG. 2 is a diagrammatical overview of an example fluidic system of the sequencing system of FIG. 1.

FIG. 2 illustrates an example fluidic system 55 of the sequencing system 10 of FIG. 1. The fluidic system 55 may be disposed onboard the instrument 12 shown in FIG. 1. In the example illustrated, the flow cell 20 includes a series of pathways or lanes 56A and 56B which may be grouped in pairs for receiving fluid substances (e.g., reagents, buffers, reaction media) during sequencing operations. The lanes 56A are coupled to a first common line 58, while the lanes 56B are coupled to a second common line 60. A bypass line 62 is also provided to allow fluids to bypass the flow cell 20 without entering it. In the illustrated example, the bypass line 62 includes a cache channel 118 along the length of the bypass line 62, which may be used for temporary storage of reagents and initial mixing of the reagents, as described in more detail herein. As noted above, a series of vessels or reservoirs 64 allow for the storage of reagents (e.g., the reagents 30 in FIG. 1) and other fluids that may be utilized during the sequencing operation.

A reagent selector/selection valve 66 is coupled to a motor or actuator (not shown) to allow selection of one or more of the reagents in the corresponding reservoirs 64 to be introduced into the flow cell 20. Selected reagents are then advanced to a common line selector/selection valve 68 which similarly includes a motor (not shown). The common line selector valve 68 may be commanded to select one or both of the common lines 58 and 60 to cause the reagents to flow to the lanes 56A and/or 56B in a controlled fashion. The common line selector valve 68 may be commanded to cause the reagents to flow through the bypass line 62 into the cache channel 118. It may be noted that other useful operations may be enabled by the bypass line 62, such as the ability to prime all reagents (and liquids) to the reagent selector valve 66 (and the common line selector valve 68) without drawing air through the flow cell 20, the ability to perform washing (e.g., automated or semi-automated washing) of various flow paths 34 independent of the flow cell 20, and the ability to perform diagnostic functions (e.g., pressure and volume delivery tests) on the system 55.

Figure 4:
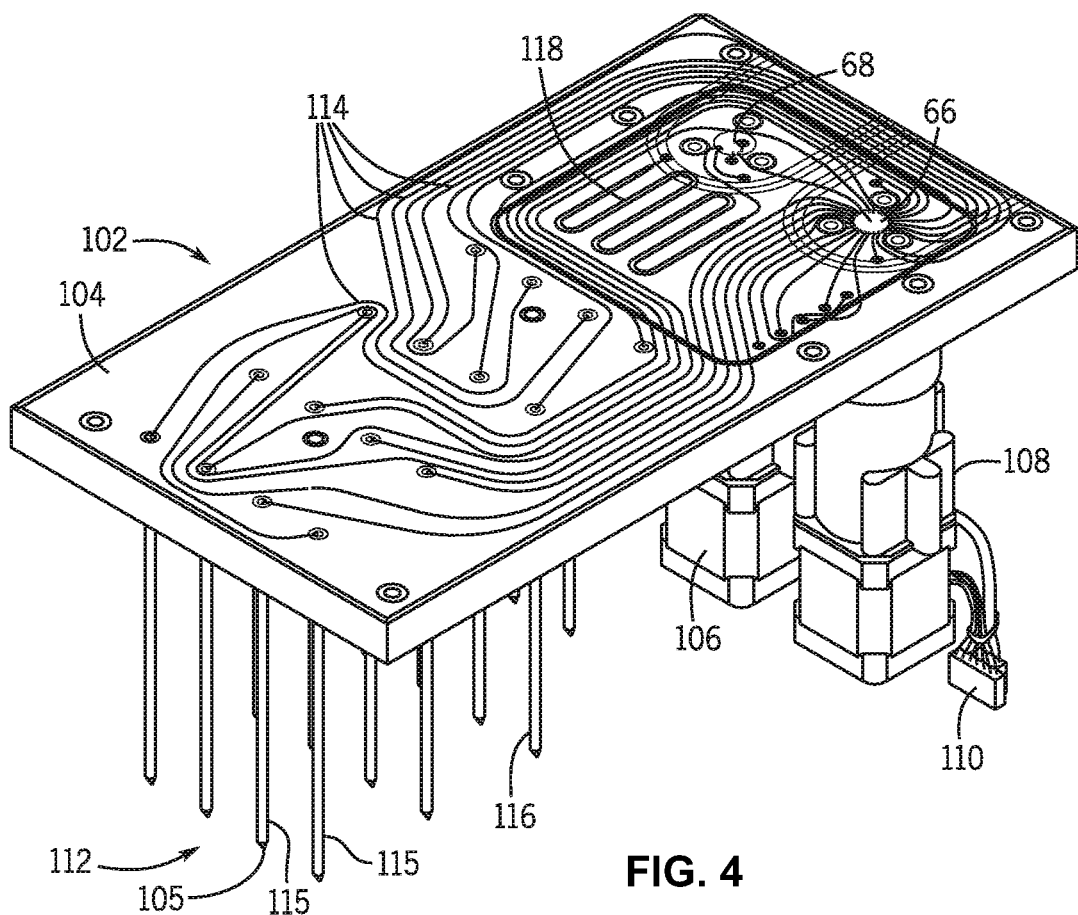
FIG. 4 illustrates a valve assembly of the fluidic system shown in FIG. 2 according to an example.
Figure 5:
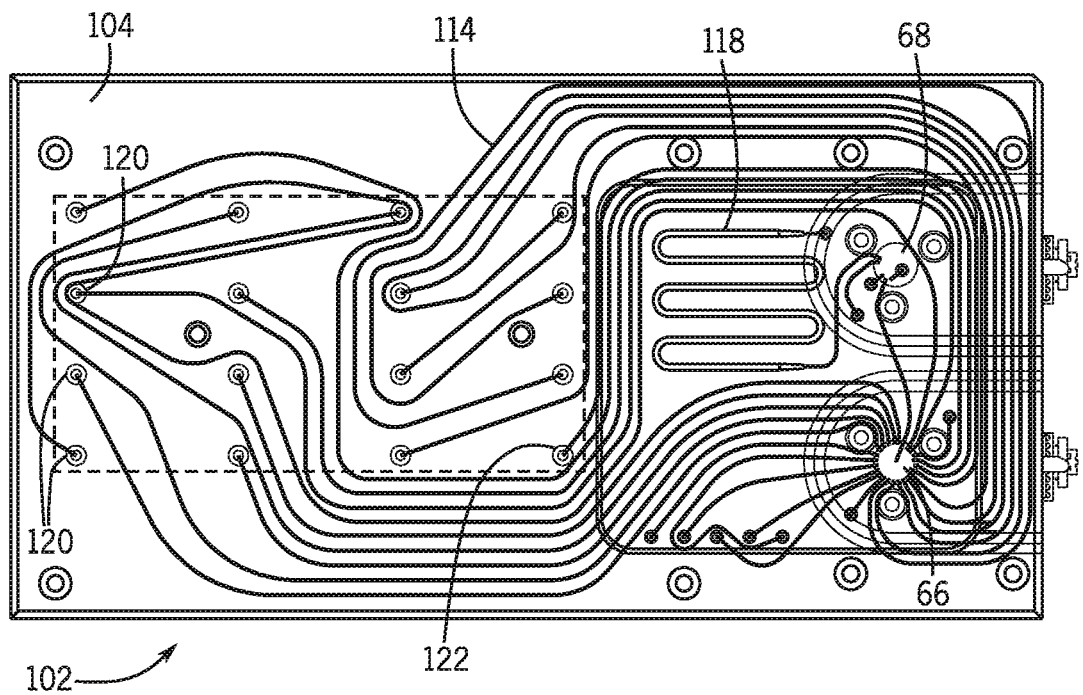
FIG. 5 is a top view of the valve assembly shown in FIG. 4.

At least some of the components of the fluidic system 55 may be contained in or disposed on a structural manifold 104. For example, the manifold 104 may include or hold the reagent selector valve 66, the common line selector valve 68, the common lines 58, 60, the bypass line 62 including the cache channel 118, and/or the like. The manifold 104 according to one example is shown in FIGS. 4 and 5.

Used reagents exit the flow cell 20 through the flow paths 36 coupled between the flow cell 20 and the pump 38. In the illustrated example, the pump 38 is a syringe pump having a pair of syringes 70 that are controlled and moved by an actuator 72 to aspirate the reagents and other fluids and to eject the reagents and fluids during different operations of the testing, verification and sequencing cycles. The pump 38 may include various other parts and components, including valving, instrumentation, actuators, and so forth (not shown). In the illustrated example, pressure sensors 74A and 74B sense pressure on inlet lines of the pump 38, while a pressure sensor 74C is provided to sense pressures output by the pump 38.

Fluids used by the system 55 enter a used reagent selector/selection valve 76 from the pump 38. The valve 76 allows for selection of one of multiple flow paths for used reagents and other fluids. In the illustrated example, a first flow path leads to a first used reagent receptacle 78, while a second flow path leads through a flow meter 80 to a second used reagent receptacle 82. Depending upon the reagents used, it may be advantageous to collect the reagents, or certain of the reagents in separate vessels for disposal, and the used reagent selector valve 76 allows for such control.

It should be noted that valving within the pump 38 may allow for various fluids, including reagents, solvents, cleaners, air, and so forth to be aspirated by the pump 38 and injected or circulated through one or more of the common lines 58, 60, the bypass line 62, and the flow cell 20.

The fluidics system 55 operates under the command of the control circuitry 46 which implements prescribed protocols for mixing, testing, verification, sequencing, and so forth. The prescribed protocols are established in advance and include a series of events or operations for various activities, such as aspirating reagents, transferring the reagents to a mixing reservoir, mixing the reagents, flowing the reagent mixture onto the flow cell 20, sequencing the molecules on the flow cell 20, obtaining data regarding the sequencing, analyzing the data, and the like. The protocols are stored in the memory circuitry 50 (shown in FIG. 1) and allow for coordination of fluidic operations, such as reagent transfer and mixing, with other operations of the instrument 12, such as reactions occurring in the flow cell 20, imaging of the flow cell 20 and its sites, and so forth. In the illustrated example, the control circuitry 46 includes one or more valve interfaces 84 which are configured to provide command signals for the valves 66, 68, as well as a pump interface 86 configured to command operation of the pump 38 (e.g., via the actuator 72). The command signals generated by the valve interface(s) 84 and the pump interface(s) 86 are generated according to specific protocols from the memory circuitry 50 that are being implemented by the control circuitry 46. Various input/output circuits 88 may also be provided for receiving feedback and processing such feedback, such as from the pressure sensors 74A-C and flow meter 80.

Figure 3:
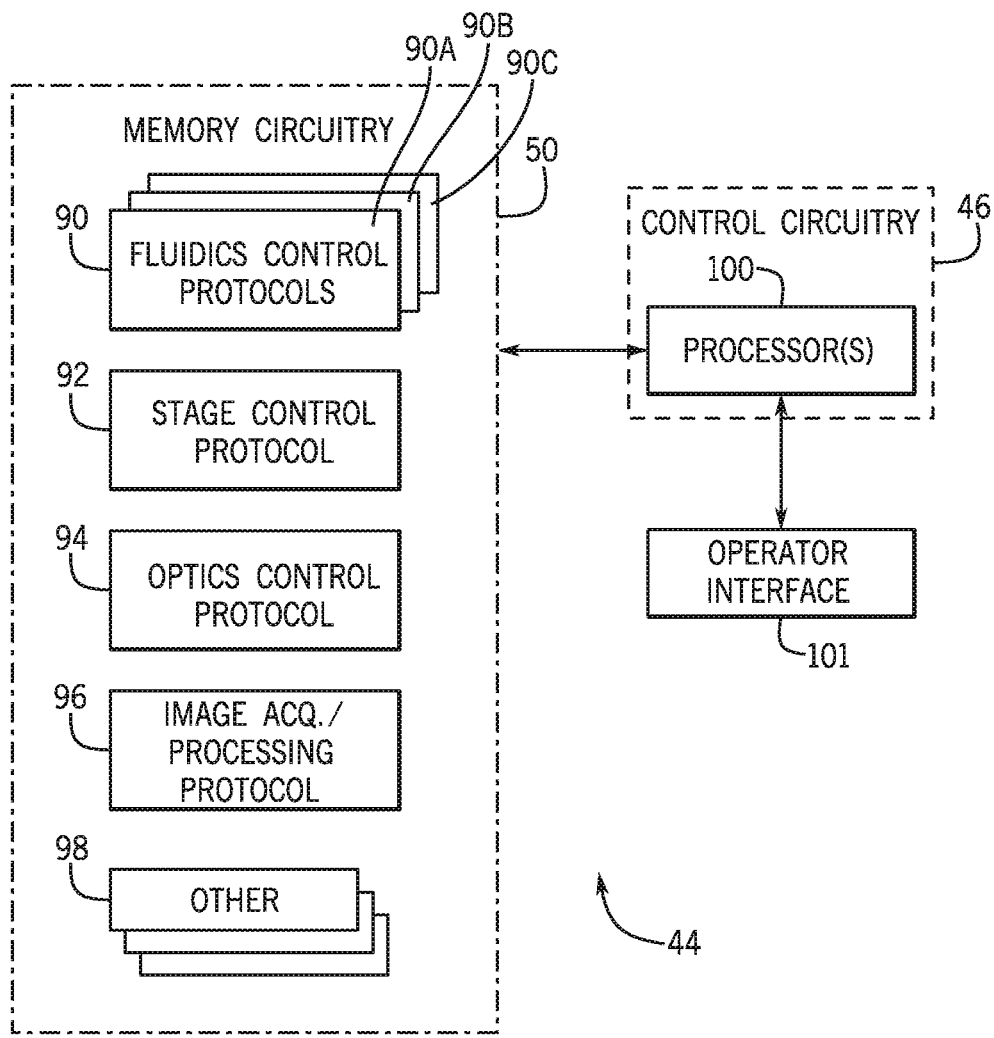
FIG. 3 is a diagrammatical overview of an example processing and control system of the sequencing system of FIG. 1.

FIG. 3 illustrates certain functional components of the control supervisory system 44. As illustrated, the memory circuitry 50 stores the protocols, which are prescribed routines that are executed during mixing, testing, commissioning, troubleshooting, servicing, and sequencing operations. Many such protocols may be implemented and stored in the memory circuitry 50, and the protocols may be updated or altered from time to time. As illustrated in FIG. 3, the protocols may include fluidics control protocols 90 for automatically controlling the various valves (e.g., the valves 66 and 68), the pumps (e.g., the pump 38), and any other fluidics actuators in the instrument 12. The fluidics control protocols 90 may represent different routines for automatically controlling reagent aspiration into a cache, reagent discharge into a mixing reservoir, mixing of the reagents with the sample template in the mixing reservoir, and flowing of the combined reagent-sample mixture to the flow cell 20. The fluidics control protocols 90 direct the operation of the valves 66 and 68 and the pump 38 to control the transfer and mixing of the reagents. The fluidics control protocols 90 may include multiple protocols 90A-C (referred to as mixing protocols) for controlling the selection, aspiration, transfer, and mixing of the reagents according to different pre-set routines. For example, the protocols 90A-C may include routines for aspirating reagents from multiple different reagent reservoirs into a cache channel in designated amounts and/or a designated sequence; then discharging the reagents from the cache channel into a mixing reservoir; and mixing the reagents with a sample template within the mixing reservoir to form a clustering mixture.

The multiple protocols 90A-C may designate specific reagents to be aspirated, specific quantities of the reagents that are aspirated during each aspiration cycle, a specific ordered sequence to which the reagents are aspirated from the different corresponding reagent reservoirs, a specific number of aspiration cycles to be performed prior to discharging the aspirated reagents into a mixing reservoir, a specific reservoir into which to discharge the reagents for mixing (e.g., a template reservoir or a different reservoir), a specific amount of time to lapse between aspiration and discharge of the reagents, a specific number of aspiration mixing cycles for mixing the reagents with the sample template, specific pressure outputs of the pump 38 during the reagent transfer and mixing operations, and the like. The first mixing protocol 90A may differ from the second and third mixing protocols 90B, 90C in one or more of the aspects listed above, such as the types of reagents that are aspirated, the timing, and/or the pump pressure outputs. The fluidics control protocol 90 to be implemented may be selected in lieu of the other protocols stored in the memory circuitry 50 based on the type of sample template to be used, the type of flow cell 20 used, a specific reagent-sample mixture (referred to herein as a clustering mixture) that is desired, or the like. Although three fluidics control (or mixing) protocols 90A-C are shown in FIG. 3, the memory circuitry 50 may store more or less than three mixing protocols. The fluidics control protocols 90 may also include routines or operations for receiving and processing feedback from fluidics sensors, such as valve sensors, flow sensors, and/or pressure sensors (e.g., 74A-C).

A stage control protocol 92 allows for moving the flow cell 20 as desired, such as during imaging. An optics control protocol 94 allows for commands to be issued to the imaging components to illuminate portions of the flow cell 20 and to receive returned signals for processing. An image acquisition and processing protocol 96 allows for the image data to be at least partially processed for extraction of useful data for sequencing. Other protocols 98 may be provided in the same or different memory circuitry 50. The memory circuitry 50 may be provided as, may include, or may be contained within one or more digital memory devices, such as a hard drive, a flash storage device, or other non-transitory, computer-readable storage mediums. The digital memory device may include both volatile and non-volatile memory circuitry. Although the memory circuitry 50 is shown as being onboard the instrument 12 in FIG. 1, alternatively, at least some of the circuitry 50 may be off-board, and communicatively connected to the control circuitry 46 onboard for providing the protocols to the control circuitry 46.

One or more processors 100 of the control circuitry 46 access the stored protocols in the memory circuitry 50 and implement the protocols on the instrument 12. As noted above, the control circuitry 46 may be part of application-specific computers, general-purpose computers, or any suitable hardware, firmware and software platform. The processors 100 and the operation of the instrument 12 may be commanded by human operators via an operator interface 101. The operator interface 101 may allow for testing, commissioning, troubleshooting, and servicing, as well as for reporting any issues that may arise in the instrument 12. The operator interface 101 may also allow for launching and monitoring sequencing operations that are performed automatically by the control circuitry 46 controlling the components of the instrument 12 according to one or more selected protocols stored in the memory circuitry 50.

FIG. 4 illustrates a valve assembly 102 of the fluidic system 55 shown in FIG. 2 according to an example. The valve assembly 102 draws reagents and other fluids (e.g., buffer fluids, the sample template, and the like) from reservoirs and delivers the reagents and other fluids to the flow cell 20 (shown in FIG. 2). The valve assembly 102 includes the manifold 104 that defines fluid channels 114 to provide flow paths for the reagents and the other fluids. The reagent selector valve 66 and the common line selector valve 68 are connected to (e.g., integrated onto) the manifold 104 in fluid connection to the fluid channels 114. As can be seen in FIG. 4, the reagent selector valve 66 and the common line selector valve 68 are driven and controlled by corresponding motors 108 and 106, respectively. One or more motor interfaces or connections 110 provide power and, where desired, signals to and from the motors 106, 108. As noted above, the motors 106, 108 (and thereby the valves 68, 66) are controlled by the control circuitry 46 during testing, commissioning, servicing, and the sequencing operation (e.g., for reagent transfer and reagent mixing).

The fluid channels 114 within the manifold 104 are fluidly connected to sippers 112. The fluid channels 114 extend between the sippers 112 and the valves 66, 68. The sippers 112 are elongated from the manifold 104 to respective distal tips 105. The sippers 112 are configured to extend into different corresponding reservoirs (e.g., the reservoirs 64 shown in FIG. 2), as described in more detail below, such that the distal tips 105 contact the reagents or other fluids in the reservoirs. During operation, the sippers 112 draw the reagents and the other fluids from respective reservoirs into the fluid channels 114 of the manifold 104. The fluid channels 114 may be formed by molding, etching, or any other suitable process to allow the reagents and other fluids to move from the sippers 112 to the valves 66, 68 when the pump 38 (shown in FIG. 2) is commanded (by the control circuitry 46) to aspirate the reagents and other fluids. At least one of the sippers 112 is configured as a nozzle sipper 116 to assist in mixing of the reagents and the sample template (that together define the clustering mixture) prior to flowing the clustering mixture on the flow cell 20. The nozzle sipper 116 aligns with and extends into a mixing reservoir. At least some of the other sippers 112 are configured as reagent sippers 115 that align with and extend into corresponding reagent reservoirs (e.g., the reagent reservoirs 124, 126, and 128 shown in FIG. 6) that are pre-loaded with different reagents therein.

The mixing reservoir may be a template reservoir 136 (shown in FIG. 6) that is pre-loaded with the sample template, or may be another reservoir that is discrete from the template reservoir 136 and the reagent reservoirs (and is not pre-loaded with the sample template or the reagents). In some examples, the mixing reservoir or volume may be a portion or all of the bypass line 62. For example, reagents may be aspirated into the bypass line 62 in a desired sequence but such that the reagents do not traverse the entire length of the bypass line (which may cause them to be routed to disposal). Once the bypass line 62 (or a portion thereof serving as the mixing reservoir or volume) has been loaded with the desired sequence of reagents, the end of the bypass line 62 through which the reagents were introduced may be switched, using a valve, so as to fluidically connect with a flow path leading to, for example, a destination recipient so that the entire set of reagents loaded into the bypass line 62 may then be expelled back out of the bypass line and into the destination recipient. In other implementations, the mixing reservoir or volume may, for example, be a destination recipient, e.g., the destination recipient to which the pre-mixed fluids are delivered, or a separate destination recipient, e.g., one that is completely empty prior to delivery of the selected reagents.

The manifold 104 also includes the cache channel 118 that is fluidly connected to the fluid channels 114 through the valves 66, 68. The cache channel 118 is located along the bypass line 62 shown in FIG. 2, and may be used to temporarily store and/or at least partially mix reagents that are drawn and moved into the cache channel 118 by the valves 66, 68 and the pump 38 (shown in FIG. 2).

FIG. 5 is a top view of the valve assembly 102 shown in FIG. 4. In operation, the reagent selector valve 66 receives the reagents that are aspirated (or drawn) from the corresponding reservoirs through the sippers 112 (shown in FIG. 4), and directs the aspirated fluids to the common line selector valve 68. The cache channel 118 is fluidly connected to the common line selector valve 68 to allow for storage and/or mixing of reagents therein. The cache channel 118 may be disposed between the common line selector valve 68 and the pump 38 (shown in FIG. 2). The manifold 104 also includes ports 120 that couple the manifold 104 (e.g., the fluid channels 114 thereof) to the sippers 112. One of the ports 120 (indicated by reference 122) is coupled to the nozzle sipper 116 to allow for injecting the reagents into a destination recipient (e.g., mixing reservoir, cache channel 118, etc.), and for drawing the reagents from the destination recipient for mixing. The destination recipient, for example, may be a container, tube, or other vessel designed to contain the reagents. The destination recipient may, for example, be used as a temporary work volume to which reagents and/or other materials may be transferred in order to prepare them for delivery, e.g., by mixing, to the flow cell. Thus, reagents and other fluids may, once prepared in the destination recipient, be transferred from the destination recipient to the flow cells 20.

Figure 6:
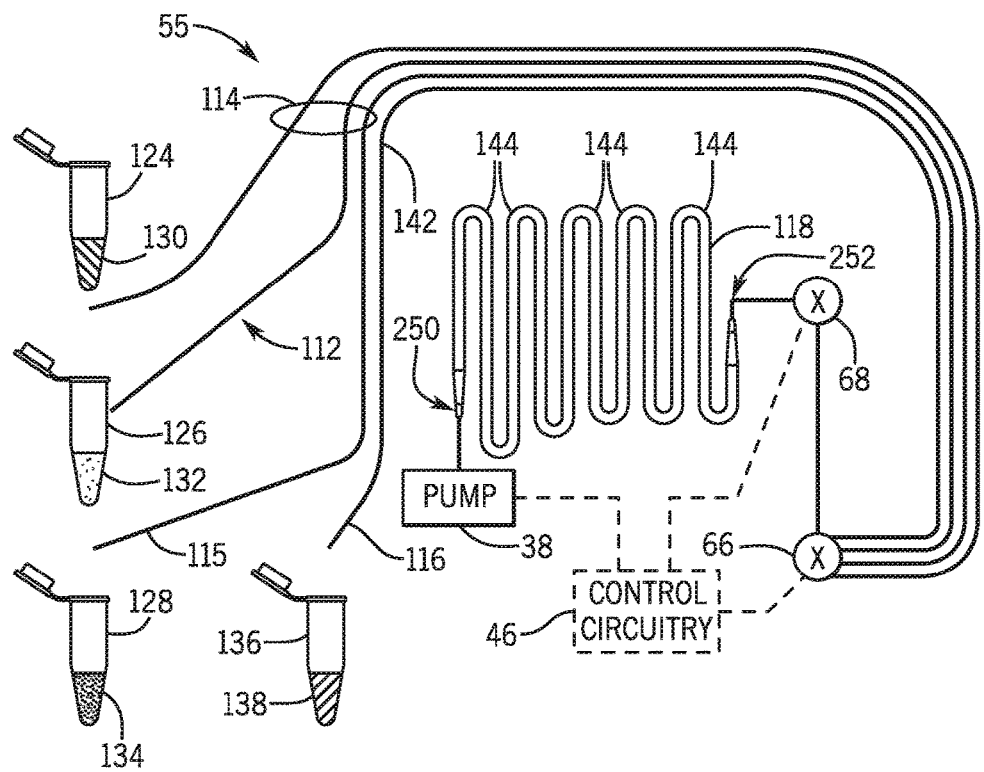
FIG. 6 illustrates a reagent mixing system according to an example.

FIG. 6 is a schematic diagram showing a portion of the fluidic system 55 according to an example. The sippers 112, the fluid channels 114, the cache channel 118, the reagent selector valve 66, the common line selector valve 68, the pump 38, and the control circuitry 46 are illustrated in FIG. 6. The fluidic system 55 also includes multiple reservoirs or vessels, which may be added to the instrument 12 (shown in FIG. 1), such as on a cartridge (not shown) inserted into the instrument 12 by an operator. The cache channel 118 extends between a pump end 250 and a reservoir end 252. The pump end 250 is operatively connected to the pump 38. For example, the pump end 250 is fluidly connected to the pump 38 such that the pump 38 is able to pneumatically apply positive and negative pressure through the cache channel 118 to move reagents and other fluids through the cache channel 118. The reservoir end 252 is fluidly connected to the sippers 112 through the valves 66, 68 and the fluid channels 114. In the illustrated arrangement, the reservoir end 252 is coupled directly to the common line selector valve 68, which is coupled to an outlet of the reagent selector valve 66, such that the common line selector valve 68 is disposed between the cache channel 118 and the reagent selector valve 66.

The cache channel 118 is designed with a larger diameter than the fluid channels 114 to allow for storing larger volumes of fluids. In an example, the cache channel 118 has a volume or capacity of about 2 mL, but may have other volumes in other examples. The larger diameter may allow the reagents therein to begin to mix together before being discharged into a mixing reservoir. However, the diameter is small enough to allow for the creation of a fluid buffer to prevent a buffer fluid in the system 55 from mixing with and diluting the reagents in the cache channel 118, as described in more detail herein. In the illustrated example, the cache channel 118 has a serpentine shape with multiple 180 degree loops or switch-backs 144. The serpentine shape may allow for a relatively large volume of reagents to be stored in a relatively compact area while the diameter is small enough to reduce dilution with the buffer fluid and maintain an ability to meter precise quantities of the reagents from the channel 118. The cache channel 118 may have other shapes in other examples.

In the illustrated example, the reservoirs include three reagent reservoirs (or vessels) 124, 126, and 128 that store reagents 130, 132, and 134, respectively, therein and one template reservoir 136 that stores a prepared sample template (or genetic library) 138 therein. The reservoirs 124, 126, 128, and 136 are shown as discrete tubes having connected lids, but the reservoirs 124, 126, 128, and 136 may be different in other examples. For example, instead of closable lids, the tubes may be sealed with a foil or foil-like material that is configured to be penetrated by the sippers 112. The reservoirs 124, 126, 128, and 136 may be inserted into a cartridge (not shown) to hold the reservoirs 124, 126, 128, and 136 in designated positions that align with the sippers 112 of the manifold 104 (shown in FIG. 4) when the cartridge is coupled to the manifold 104. Optionally, instead of discrete tubes or other vessels, at least some of the reservoirs 124, 126, 128, and 136 may be defined as cavities integral to a structure, such as the cartridge. Although shown as having approximately the same sizes and approximately the same pre-filled quantities of fluids (e.g., reagents and sample template) therein, at least some of the reservoirs 124, 126, 128, and 136 may have different sizes, shapes, and/or quantities of fluids therein (prior to extracting the fluids from the reservoirs). Furthermore, although three reagents 130, 132, and 134 are shown in the illustrated example, other examples may include only two reagents or at least four reagents that are mixed to form a reagent mixture.

The different reagents 130, 132, and 134 include at least some different reagent components relative to one another. Due to stability issues from long-term exposure to other reagents, storing the reagents separately in the different reagent reservoirs 124, 126, and 128 until ready for use may increase the usable lifespan of the reagent mixture and/or the achievable performance of the sequencing operation. In one example, the reagents can be any suitable materials. For example, the first reagent may be any mixture having a specific gravity of about 1.01 to about 1.1. The second reagent may be any mixture having a specific gravity of about 1.05 to about 1.15. The third reagent may be any mixture having a specific gravity of about 1.01 to about 1.1. In another example, the reagents can be any suitable materials. For example, the first reagent may be any mixture having a viscosity of about 1.5 cP to about 4 cP at 25° C. The second reagent may be any mixture having a specific viscosity of about 5 cP to about 10 cP at 25° C. The third reagent may be any mixture having a viscosity of about 10 cP to about 50 cP at 25° C.

As an example, the first reagent 130 in the reservoir 124 may include at least one biochemical molecule. The biomolecule can include a nucleotide (e.g., a nucleoside triphosphate (NTP)) and/or a protein. The protein may include polymerase, single stranded binding protein, helicase, topoisomerase, primase, telomerase, ligase, recombinase, or the like. The protein may function as an enzyme. As an example, the second reagent 132 in the reservoir 126 may include a biomolecule, such as a protein. The protein in the second reagent 132 may be one or more of the aforementioned proteins. As an example, the third reagent 134 in the reservoir 128 may include magnesium and a crowding agent. The crowding agent may be dextran, FICOLL® (a neutral, highly branched, high-mass, hydrophilic polysaccharide, available from GE Healthcare Life Sciences), polyethylene glycol (PEG), polyvinyl alcohol (PVA), or a protein, such as hemoglobin or ovalbumin. Crowding agents alter the properties of molecules in a solution because, due to the size and/or concentration of the crowding agents, the volume of solvent available for other molecules in the solution is reduced. The reagents 130, 132, and 134 may be any combination of any of the aforementioned molecules and may include different components and/or different distributions of the listed components in other examples. The three reagents 130, 132, 134 may have one or more components in common, such as water, a surfactant, and/or the like.

Due to the different component formulations, the reagents 130, 132, and 134 may have different fluid properties that pose challenges for automated transfer and mixing of the reagents. For example, the reagents 130, 132, and 134 may have different densities, viscosities, and oil interfacial tensions, such that the miscibility of the reagents is a challenge. As an example, the viscosities of the different reagents may range from approximately 1.5 cP to approximately 50 cP at 25° C., while oil interfacial tensions may range from about 5.0 dynes/cm to about 19.2 dynes/cm. Therefore, if the reagents and the sample template are combined without mixing, the different reagents and the sample template could be visible in the mixing reservoir 136 as distinct striations.

Reagents that have a relatively high viscosity pose challenges for the automated transfer of the reagents because the higher viscosity reagents increase pressure within the system or instrument 12 (shown in FIG. 1). The higher pressure may cause the pump 38 to increase output to move the reagents through the system, which may increase energy usage as well as enhance the risk of leaks or damage in the closed system (relative to lower pressures associated with lower viscosity reagents). In an example, at least some of the reagents 130, 132, 134 are formulated with a reduced viscosity relative to conventional reagents. For example, one or more of the reagents 130, 132, 134 may include a low molecular weight crowding agent, as opposed to a crowding agent with a greater molecular weight. A low molecular weight crowding agent may be a molecule that has a molecular weight of less than about 11,000 Daltons (Da), such as about 10,000 Da, such as about 9,000 Da, such as about 8,000 Da, such as about 7,000 Da. The crowding agent used in one or more of the reagents 130, 132, 134 according to one or more of the examples described herein may be dextran, FICOLL®, polyethylene glycol, or a protein, such as hemoglobin or ovalbumin. The low molecular weight crowding agent is considerably lower than the molecular weight of crowding agents used in some known reagents, which may be over 30,000 Da. The use of the low molecular weight crowding agent may reduce the viscosity of the corresponding reagents relative to the known reagents with higher molecular weight crowding agents. The reduced viscosity may reduce system pressure in the instrument 12 and allow for improved transfer and mixing of the reagents 130, 132, 134.

In an example, a surfactant is introduced to one or more of the reagents 130, 132, and 134 to increase the miscibility of the reagents having different fluid properties. The surfactant may be added to, or contained within, all of the reagent reservoirs 124, 126, and 128. The surfactant may be polysorbate 20, commonly referred to as TWEEN® 20 (which is a registered trademark of Croda Americas), and/or other commercially available surfactants or detergents. The use of the surfactant in the reagents may improve the mixing efficiency of the reagents, such that a substantially homogenous mixture can be achieved with less mixing (e.g., fewer mixing cycles, less mixing intensity, less mixing time, less protein fowling, etc.) relative to mixing the reagents without the surfactant. The use of the surfactant in the reagents may also reduce friction between the molecules of the reagents and various surfaces in the system relative to forming the reagents without the surfactant, which may allow for better fluid transport and less molecule-surface interactions.

During a transfer stage, the fluidic system 55 is configured to transfer the reagents 130, 132, and 134 from the respective reservoirs 124, 126, and 128 to a temporary storage vessel for pre-mixing to define a reagent mixture, and then transfers the reagent mixture to a mixing reservoir where the reagent mixture is mixed with the sample template 138. The control circuitry 46 communicates command or control signals to the valves 66, 68 and the pump 38 to automatically control the transfer and mixing of the reagents 130, 132, 134 through the system 55 according to a selected one of the mixing protocols 90 (shown in FIG. 3) that are stored in the memory circuitry 50 (FIG. 3).

In an example, the temporary storage vessel used for pre-mixing the reagents 130, 132, and 134 is the cache channel 118. For example, the reagents 130, 132, and 134 are aspirated (or drawn) from the respective reservoirs 124, 126, and 128 into the cache channel 118 through the corresponding sippers 115 that extend into the reservoirs. The pump 38 and the reagent selector valve 66 are controlled to aspirate each reagent through the corresponding sipper 115 along the corresponding fluid channel 114 into the cache channel 118 through the reservoir end 252. As described in more detail below, the reagents 130, 132, and 134 are aspirated as designated amounts of the reagents, which may or may not be the same between the different reagents. The reagents 130, 132, 134 may be aspirated one at a time in an ordered sequence, which optionally may be repeated one or more times, either before or after discharging the reagents from the cache channel 118 (according to the protocol that is being implemented). As a result, the cache channel 118 may have an alternating pattern of the reagents 130, 132, 134 along a length of the cache channel 118.

After a designated volume of each of the reagents 130, 132, 134 is aspirated into the cache channel 118, at least some of the reagent mixture is discharged from the cache channel 118 into a mixing reservoir, where the reagent mixture is mixed with the sample template. In the illustrated example, the mixing reservoir is the template reservoir 136 that is pre-loaded with the sample template therein. In an alternative example, however, the mixing reservoir may be different than the template reservoir 136. For example, the mixing reservoir may be one of the reagent reservoirs 124, 126, or 128, such that the reagent mixture is discharged from the cache channel 118 into one of the reagent reservoirs for mixing. In another alternative example, the mixing reservoir may be a designated mixing reservoir that is different from the reagent reservoirs and the template reservoir. In such an example, the sample template may be aspirated from the template reservoir 136 similarly to the aspiration of the reagents 130, 132, 134, and subsequently discharged into the designated mixing reservoir before or after discharging the reagent mixture into the mixing reservoir.

The reagent mixture is discharged into the mixing reservoir by controlling the pump 38 and the reagent selector valve 66 to propel the reagent mixture to the nozzle sipper 116 via a fluid channel 142 that connects the nozzle sipper 116 to the reservoir end 252 of the cache channel 118. During a mixing stage, the reagent mixture is mixed with the sample template within the mixing reservoir to form a clustering mixture that is subsequently flowed to the flow cell 20 (shown in FIG. 2). Therefore, the fluidic system 55 allows for the reagents to be automatically selectively aspirated one-by-one into the cache channel 118, injected into the mixing reservoir, and mixed with the sample template, prior to flowing to the flow cell 20.

Figure 7:
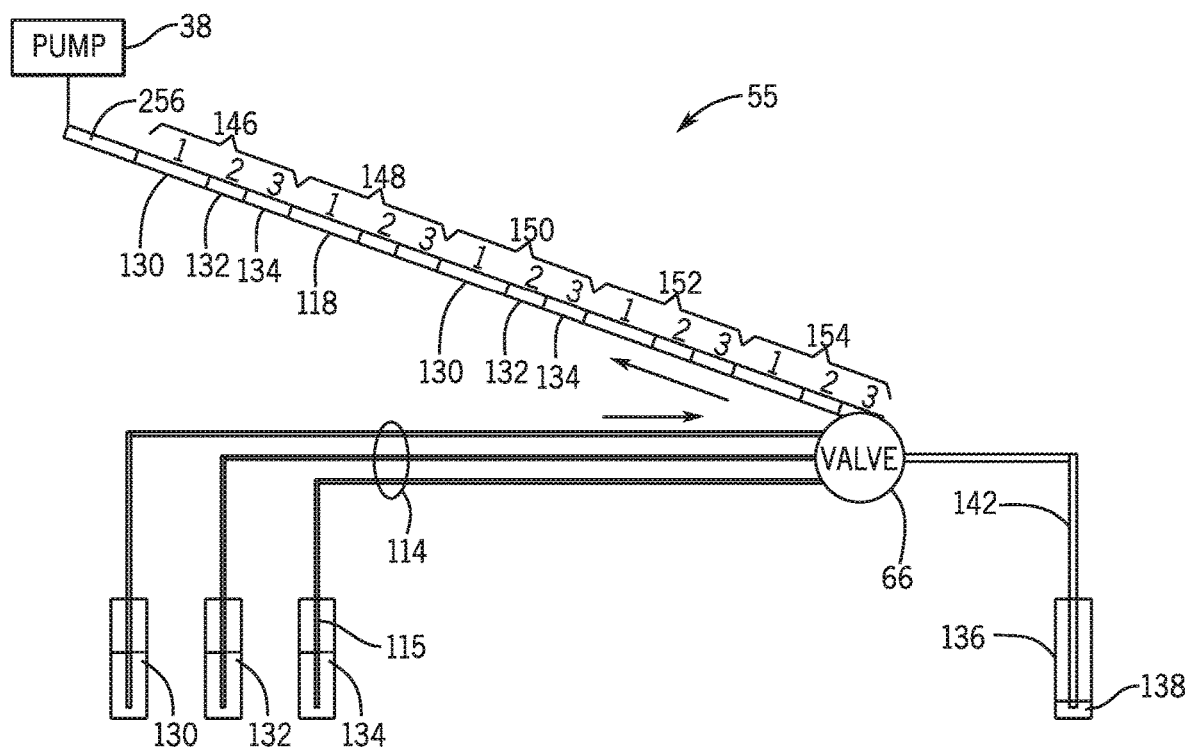
FIG. 7 illustrates a schematic diagram of the reagent mixing system according to an example.

FIG. 7 illustrates a schematic diagram of the fluidic system 55 according to an example. The serpentine cache channel 118 is illustrated as linear in the schematic diagram for clarity of description. In an example, during the transfer (or transport) stage, the fluidic system 55 is wet, such that the cache channel 118 is filled with a liquid buffer fluid 256 that is used for pneumatically manipulating (e.g., pushing) the reagents, and may also be used for priming, washing, and the like. The pump 38 and the reagent selector valve 66 are controlled by the control circuitry 46, and more specifically by the pump interface 86 and the valve interface 84 thereof, which are shown in FIG. 2.

In an aspiration operation, the control circuitry 46 controls the common line selector valve 68 (shown in FIG. 6) to direct the reagents 130, 132, 134 to the cache channel 118. The control circuitry 46 controls the reagent selector valve 66 to select one or more of the different reagents 130, 132, 134 at a time in an ordered sequence, as designated by the selected mixing protocol 90 that is implemented. The pump 38 is controlled to provide a negative pressure that sucks or draws the selected reagent or reagents into the corresponding sippers 115. In the illustrated example, the selector valve 66 is controlled to aspirate specific, measured volumes of the reagents one at a time in a sequence that includes the first reagent 130, then the second reagent 132, then the third reagent 134. Aspirating the reagents in the sequence results in a set of volumes of the reagents in the cache channel 118.

In an example, the pump 38 and selector valve 66 are controlled to repeat the aspiration of the reagents in the ordered sequence at least once, resulting in multiple sets of the reagents in the cache channel 118 concurrently. For example, in the illustrated example, the sequence is repeated four additional times such that the cache channel 118 includes five sets of the reagents, as indicated by reference numerals 146, 148, 150, 152, and 154. The set 146 is the first set aspirated, and is located between the buffer fluid 256 and the set 148. Although the reagents are aspirated in five rounds or cycles in FIG. 7 according to an example mixing protocol, the pump 38 and selector valve 66 may be controlled according to other protocols to perform more or less aspiration cycles. For example, according to another protocol, the reagents may be aspirated in seven rounds such that the cache channel 118 concurrently holds seven sets of the reagents prior to discharging the reagents. The pump 38 and reagent selector valve 66 are controlled to draw designated amounts of the reagents, which may or may not be equal. For example, the designated amount of the first reagent 130 may exceed the designated amount of the second reagent 132 in each set, as indicated by the longer length of the segment representing reagent 130 (labeled "1") compared to the length of the segment representing reagent 132 (labeled "2") in the sets 146, 148, 150, 152, and 154.

Due to the multiple aspiration cycles, the cache channel 118 contains an alternating pattern of the reagents 130, 132, 134 along the length of the cache channel 118. The reagents 130, 132, and 134 may start to mix together within the cache channel 118 at the interfaces between the amounts of the different reagents 130, 132, and 134. Therefore, the reagents 130, 132, and 134 may pre-mix within the cache channel 118 prior to mixing in the mixing reservoir. During the time that the reagents 130, 132, and 134 are aspirated and held in the cache channel 118, the mixing reservoir (which is the template reservoir 136 in the illustrated example) contains only the sample template 138. As described above, the sample template 138 includes nucleic acids of a DNA library or other genetic material. The template reservoir 136 may be pre-loaded with the sample template 138. Once aspirated as illustrated in FIG. 7, the reagent selector valve 66 can then be controlled by the control circuitry 46 according to a mixing protocol 90 to allow the pump 38 to inject or discharge the reagents 130, 132, and 134 from the cache channel 118 into the template reservoir 136 for mixing with the sample template 138 therein.

Figure 8:
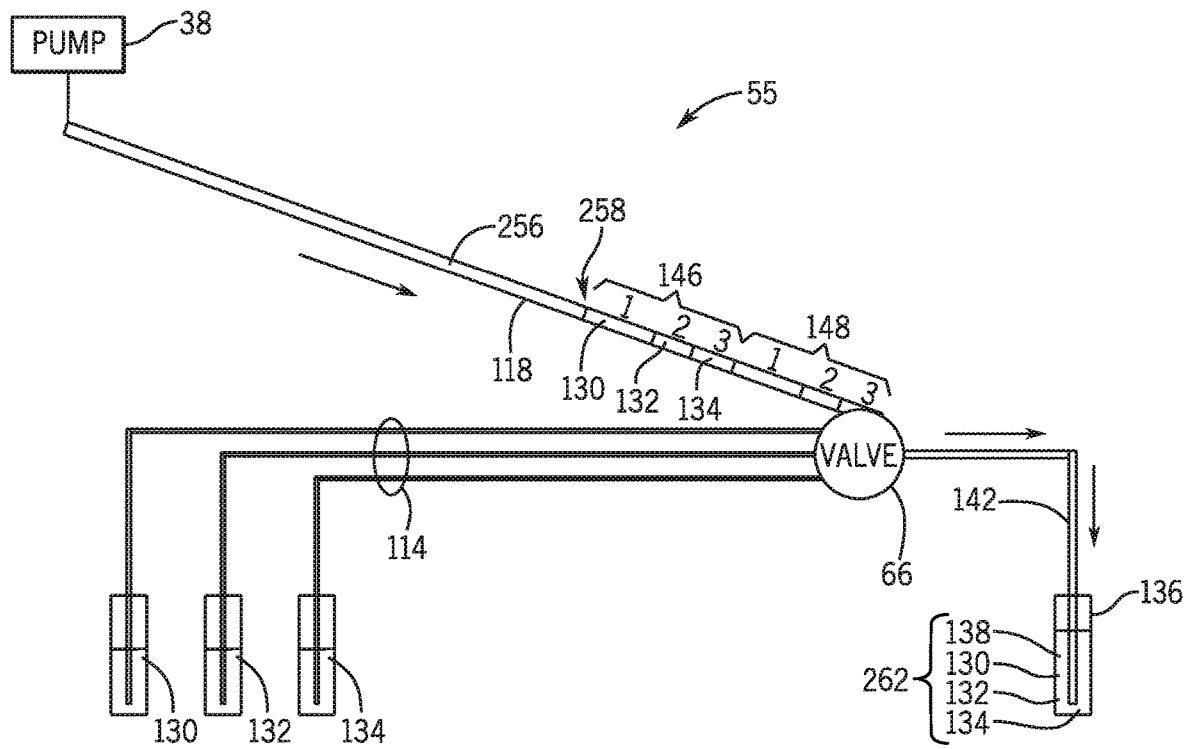
FIG. 8 illustrates the schematic diagram of the reagent mixing system shown in FIG. 7 after discharging some of the reagent mixture into the template reservoir.

FIG. 8 illustrates the schematic diagram of the fluidic system 55 shown in FIG. 7 after discharging some of the reagent mixture into the template reservoir 136. To discharge the reagent mixture from the cache channel 118 into the reservoir 136 for mixing according to a selected mixing protocol 90, the pump 38 is controlled by the control circuitry 46 to produce a positive pressure that pushes the reagent mixture towards the reagent selector valve 66. The reagent selector valve 66 is actuated to guide the reagent mixture along the fluid channel 142. The reagent mixture is discharged through the nozzle sipper 116 into the template reservoir 136, and mixes with the sample template 138 in the reservoir 136. The reagents 130, 132, and 134 combine with the sample template 138 to form a clustering mixture 262 that is fully mixed and at least substantially homogeneous after a subsequent mixing process.

In the illustrated example, less than the full aspirated amount of the reagents 130, 132, and 134 is discharged from the cache channel 118 into the template reservoir 136. For example, although five sets 146, 148, 150, 152, and 154 of the reagents 130, 132, and 134 were drawn into the cache channel 118, not all five sets are discharged into the reservoir 136. As shown in FIG. 8, two of the sets 146 and 148 remain in the cache channel 118 after discharging the sets 150, 152, and 154 into the reservoir 136, and therefore define a residual volume of the reagents 130, 132, and 134. The sets 146 and 148 are retained in the cache channel 118 to avoid the risk of diluting the reagents 130, 132, and 134 that are discharged into the template reservoir 136. Since the set 146 contacts the buffer fluid 256 at a fluid interface 258, there is a risk that the buffer fluid 256 may mix with the reagents 130, 132, and 134, thereby diluting the reagents 130, 132, and 134. To maintain designated concentrations of the reagents 130, 132, and 134 in the reagent mixture that is injected into the reservoir 136, the set 146 at the fluid interface 258 and the set 148 adjacent to the set 146 are sacrificed and used to create an upstream buffer zone that separates the buffer fluid 256 from the volume of the reagent mixture (e.g., the sets 150, 152, and 154) that is discharged into the reservoir 136. In an alternative example, one set or at least three sets of the reagents 130, 132, and 134 may be sacrificed to form the upstream buffer zone. The amount of reagents 130, 132, and 134 sacrificed to form the upstream buffer zone may be independent of the total number of sets of reagents 130, 132, and 134 aspirated into the cache channel 118. For example, if seven sets of reagents 130, 132, and 134 were aspirated into the cache channel 118, five of the seven sets may be discharged into the mixing reservoir to form the upstream buffer zone with the two remaining sets.

Optionally, the process of aspirating the reagents from the different reagent reservoirs and then subsequently discharging at least some of the aspirated volume of the reagents into the mixing reservoir may be repeated according to the selected mixing protocol 90. For example, in one example, after discharging the volume of the reagents 130, 132, and 134 within the sets 150, 152, and 154 into the template reservoir 136, the pump 38 and the reagent selector valve 66 may be controlled to aspirate one or more additional sets of the reagents in the same ordered sequence that is shown in FIG. 7. In one example, two more sets (not shown) are drawn into the cache channel 118, such that the channel 118 holds four reagent sets (e.g., including the sets 146 and 148 used for the upstream buffer zone). Subsequently, the pump 38 and the reagent selector valve 66 are controlled to discharge the two additional sets of reagents into the template reservoir 136 (without discharging the reagents used as the buffer zone). In an alternative example, the process of aspirating the reagents is performed only once, such that the total number of sets of reagents to be discharged into the mixing reservoir is aspirated into the cache channel 118 during a single time period prior. For example, seven sets of reagents are aspirated into the cache channel 118 for discharging five of the seven sets into the mixing reservoir instead of aspirating five sets, then discharging three sets before aspirating and discharging two additional sets.

The volume amounts of the reagents aspirated in each set and the number of sets aspirated may be controlled to result in a predefined volume of the reagent mixture within the template reservoir 136. The predefined volume of the reagent mixture has a predefined volumetric ratio of the different reagents therein. By aspirating the reagents from the reagent reservoirs instead of dumping the reagent reservoirs into the mixing reservoir, a more precise volume and ratio of the reagents can be achieved in the reagent mixture relative to relying on the pre-loaded volumes of the reagents within the reagent reservoirs.

Figure 9:
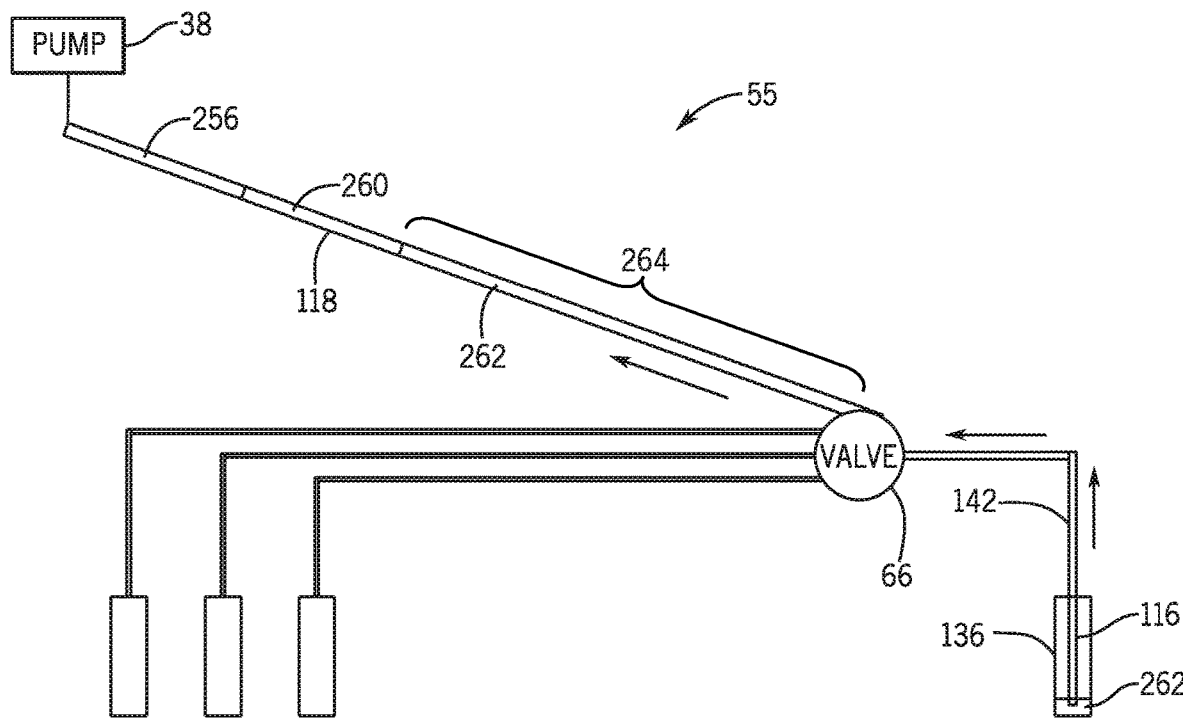
FIG. 9 illustrates the schematic diagram of the reagent mixing system during the mixing stage according to an example.

FIG. 9 illustrates the schematic diagram of the fluidic system 55 during the mixing stage according to an example. Due to the different fluid properties of the reagents and the sample template, the clustering mixture 262 is actively mixed within the template reservoir 136 according to the selected mixing protocol 90 to make the clustering mixture 262 homogenous (or generally homogenous). In one example, the clustering mixture 262 is mixed by aspirating a volume or amount 264 of the clustering mixture 262 into the cache channel 118 through the nozzle sipper 116 and subsequently discharging the volume 264 of the clustering mixture 262 back into the template reservoir 136. The aspiration and discharge process promotes vorticity in the template reservoir 136 that provides efficient mixing of the clustering mixture 262.

Prior to aspirating the clustering mixture 262, the pump 38 and the valve(s) 66 may be controlled to de-prime the fluidic system 55 with air. The de-priming process may involve the use of the pump 38 to draw air into the fluid lines, such as in the cache channel 118, the fluid channel 142, and/or the nozzle sipper 116. As shown in FIG. 9, when the clustering mixture 262 is drawn into the cache channel 118, the clustering mixture 262 is spaced apart from the buffer fluid 256 by an air gap 260. The air gap 260 separates the buffer fluid 256 from the clustering mixture 262, preventing the buffer fluid 256 from mixing with and diluting the clustering mixture 262. The de-priming step to introduce air into the system may inhibit the ability of the system to accurately aspirate specific volumes of fluids, but such accurate measuring is not necessary during the mixing stage. For example, the volume 264 of the clustering mixture 262 does not have to be a specific, accurately-measured amount, as the volume 264 is subsequently injected back into the reservoir 136. Therefore, in an example, the system may be primed (or without air) during the transfer stage in which the reagents are aspirated, and the system may thereafter be de-primed (to introduce air) during the mixing stage. The air is used to provide a buffer at the air gap 260 that prevents diluting the clustering mixture 262. During the discharge of the volume 264 of the clustering mixture 262 back into the reservoir 136, the full amount of the volume 264 is ejected through the nozzle sipper 116 as well as a portion of the air from the air gap 260. The air injected into the reservoir 136 may increase the vorticity in the reservoir 136 beyond what is provided by the discharge of the liquid mixture 262. The air is used to provide a buffer for the mixing process instead of creating an upstream buffer zone by sacrificing a portion of the reagent mixture, which is used during reagent transfer, because of relatively high fluid velocities that are involved to induce mixing. For example, higher fluid velocities may be achieved using the air as a buffer instead of using a portion of the reagent mixture as a buffer.

In another technique in which three or more reagents may be selected for mixing in the destination recipient (e.g., mixing reservoir or cache channel 118), at least two of the reagents selected for mixing may be repeatedly introduced one-by-one into the mixing channel, with at least one other reagent selected for mixing being held in reserve until the reagents that are repeatedly introduced one-by-one to the mixing reservoir have been fully delivered to the mixing reservoir. The reserved reagent may then be added all at once to the mixing reservoir. For example, if reagents A and B are to be repeatedly introduced one-by-one into the mixing reservoir, followed by reserved reagent C, then the reagents in the mixing reservoir would generally be layered as ABABABABABC, as opposed to ABCABCABCABCABC (which would result from, for example, a technique similar to that discussed with respect to FIG. 7). Such a technique is believed to be advantageous in preventing or reducing the occurrence of, for some reagents, undesired reaction byproducts. For example, the reserved reagent may react with one of the other reagents in isolation in one particular manner, but may react with two or more of the other reagents in combination in another manner. The latter may be the desired reaction that may occur once the reagents have been thoroughly mixed, whereas the former may occur during pre-mixing when the reagents may still be relatively stratified and may only mix with the directly adjacent neighboring reagent. In another example, the reserved reagent may react with the material that forms the structure of the mixing reservoir and produce an undesired byproduct. Since the repeated one-by-one introduction of reagents to the mixing reservoir may require several minutes, e.g., 5 minutes, 10 minutes, 15 minutes, or longer, depending on the number and quantity of each reagent desired, reserving the introduction of potentially troublesome reagents until after the other reagents have been delivered one-by-one to the mixing reservoir may significantly reduce the amount of time that the reserved reagent spends in contact with the other reagents and with the structure of the mixing channel, thereby reducing the potential for undesirable reaction byproducts to be generated. Of course, in such implementations, the reserved reagent may not benefit from the pre-mixing that the other reagents benefit from, but the reduced potential for undesirable reaction byproducts may outweigh the loss of the pre-mixing with respect to the reserved reagent. In particular, if the reserved reagent is a lower-viscosity liquid, the loss of pre-mixing with respect to the reserved agent may ultimately have little impact.

The use of a channel-like mixing volume, e.g., a volume that is much longer in length than it is wide (for example, at least 10×, 100×, 150× to 170×, 160×, 200×, or 500× longer than it is wide) may allow the serially-delivered reagents to maintain a relatively stratified arrangement relative to one another within the channel by reducing the surface-to-surface contact interface area between each layer of reagents (the reagents are liquid and will thus likely diffuse into each other across this boundary to some extent over time, so the boundary/contact interface areas referenced herein are to be understood to be theoretical in nature; reducing these theoretical areas will, however, slow the rate of diffusion). In addition, for reagents that may be somewhat immiscible with one another, a mixing volume that is, for example, spherical in shape or that has a larger width-to-length ratio may allow the various reagent doses that are delivered into the mixing volume to float within the mixing volume and potentially re-combine with earlier doses of that same reagent, thereby losing the stratification that may be achieved in a channel-like mixing volume. For example, a mixing channel that is approximately 2.25 mm in diameter or width for approximately 360 mm of its length may provide advantageous stratification in delivered reagents during the pre-mixing process. Once the mixing volume has been loaded with the desired quantities of the multiple sets of reagents, the contents of the mixing volume may be delivered to the destination recipient (some portion of the fluids in the mixing volume may be lost to the dead volume of the fluidic system; the total volume of the reagents delivered to the mixing volume may be calibrated to account for such loss). After delivery to the destination recipient, the delivered pre-mixed reagents may be repeatedly aspirated from and ejected back into the destination recipient to promote further mixing. In some implementations, the pre-mixed (or post-pre-mixed) reagents may be aspirated from the destination recipient and pulled back into the mixing volume before being ejected back into the destination recipient. Thus, in such implementations, the pre-mixed reagents may be moved into and out of the mixing volume repeatedly during the aspiration/ejection mixing operation.

Figure 10:
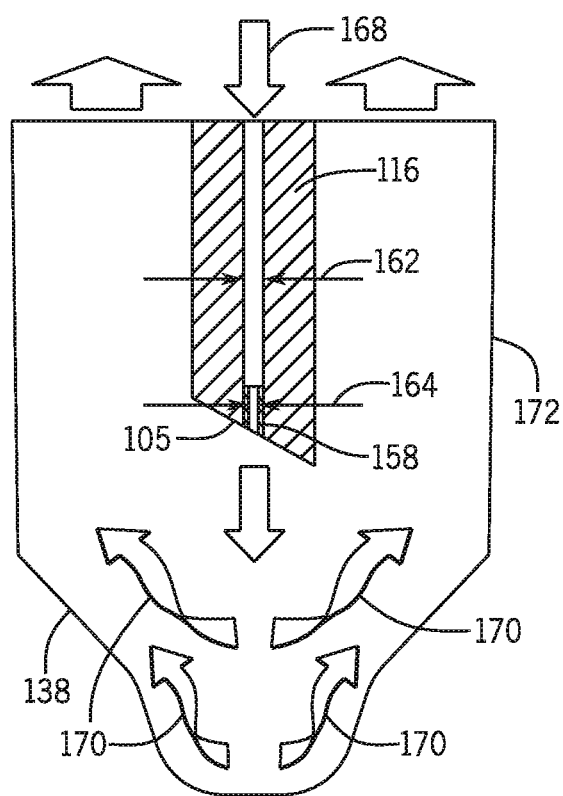
FIG. 10 illustrates a close-up portion of the nozzle sipper within a mixing reservoir according to an example.

It has been found that the use of the mixing volume/channel with a nozzle sipper 116 that promotes vorticity in the destination recipient and provides excellent mixing of reagents and the template despite substantial differences in fluid properties of the reagents. Moreover, these structures and techniques enable automated mixing with little or no human interaction. FIG. 10 illustrates a close-up portion of the nozzle sipper 116 within a mixing reservoir 172 according to an example. The nozzle sipper 116 may have an elongated body with a central lumen (cavity, channel) extending along its length. The nozzle sipper 116 may be designed to discharge the clustering mixture into the mixing reservoir 172 at a velocity that provides enhanced mixing of the clustering mixture. For example, the nozzle sipper 116 may have a smaller inner diameter compared to the inner diameters of the reagent sippers 115, which allows for an increased flow rate through the nozzle sipper 116 (relative to the reagent sippers 115). In an example, the reduced inner diameter may be provided by a nozzle insert 158 that is loaded into the central lumen of the nozzle sipper 116 at the distal tip 105 to reduce the size of the lumen/channel through the sipper 116. For example, the nozzle sipper 116 may have a nominal inner diameter 162 of about 0.020 inches (0.508 mm), while the nozzle insert 158 has a nominal inner diameter 164 of about 0.010 inches (0.254 mm). In some examples, the nozzle sipper 116 has a nominal outer diameter of about 0.125 inches (3.175 mm) and a nominal inner diameter 162 of 0.020 inches±0.001 inches, while the nozzle insert 158 has a nominal inner diameter 164 of 0.010 inches±0.001 inches (0.254 mm, although some implementations may feature a nozzle inner diameter 164 ranging from 0.20 mm to 0.28 mm). Of course, other sizes and dimensions may be utilized to provide the desired mixing. In an alternative example, the nozzle sipper 116 does not include the nozzle insert 158 therein.

The nozzle insert 158 may have any suitable shape that is compliant with the shape of the distal end 105 of the nozzle sipper 116.

In the illustrated implementation, the nozzle sipper 116 is positioned at a height above the bottom of the reservoir 172 (such as approximately 2 mm from the bottom). As the clustering mixture is injected into the reservoir 172 along the direction 168, the vorticity of the mixture within the reservoir 172 is enhanced by virtue of the increased velocity of the mixture moving through the nozzle 158, thereby enhancing mixing, as indicated by arrows 170.

Figure 11:
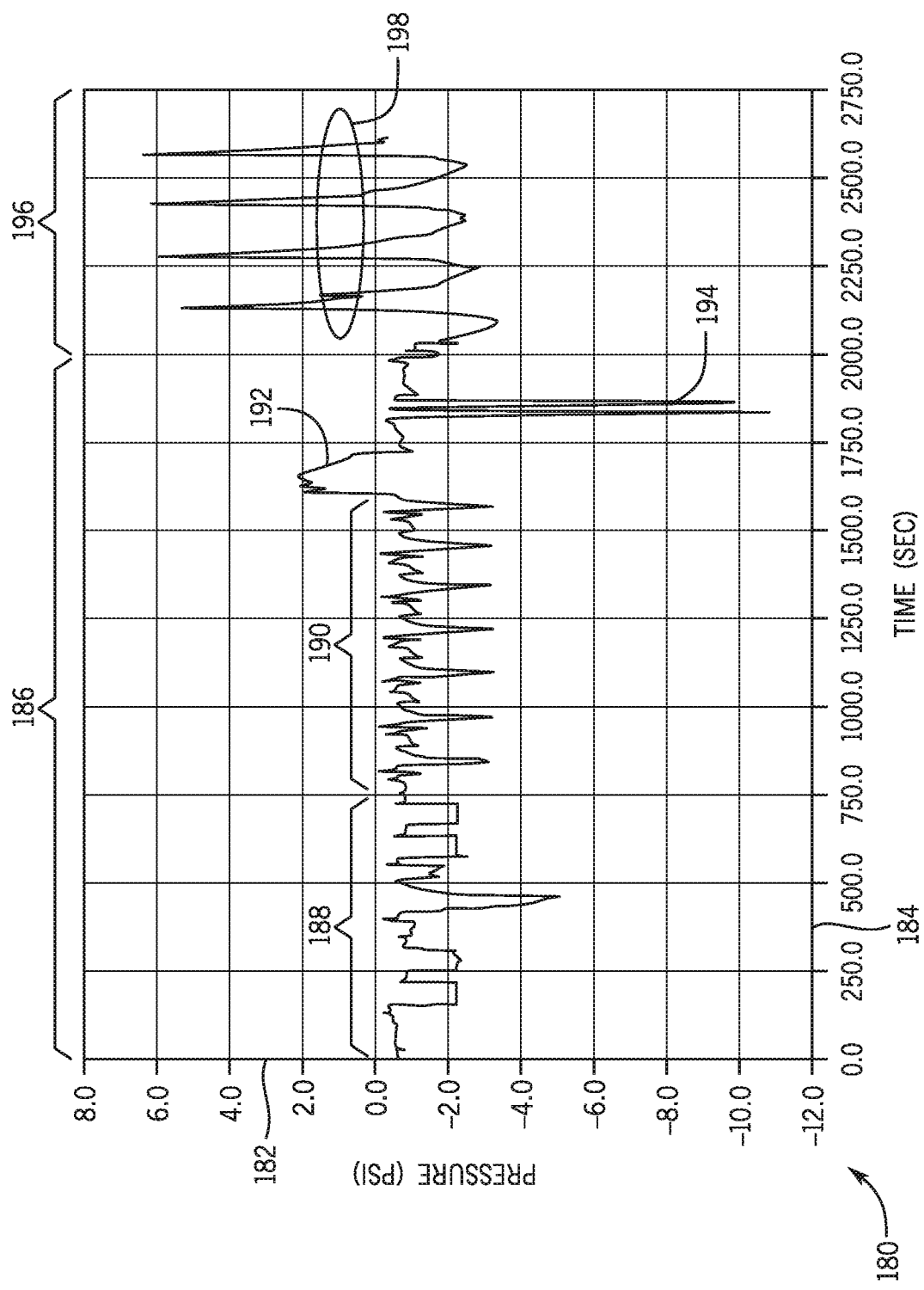
FIG. 11 is a graphical representation of an example cycle in aspirating and mixing reagents and a sample template according to an example.
Figure 12:
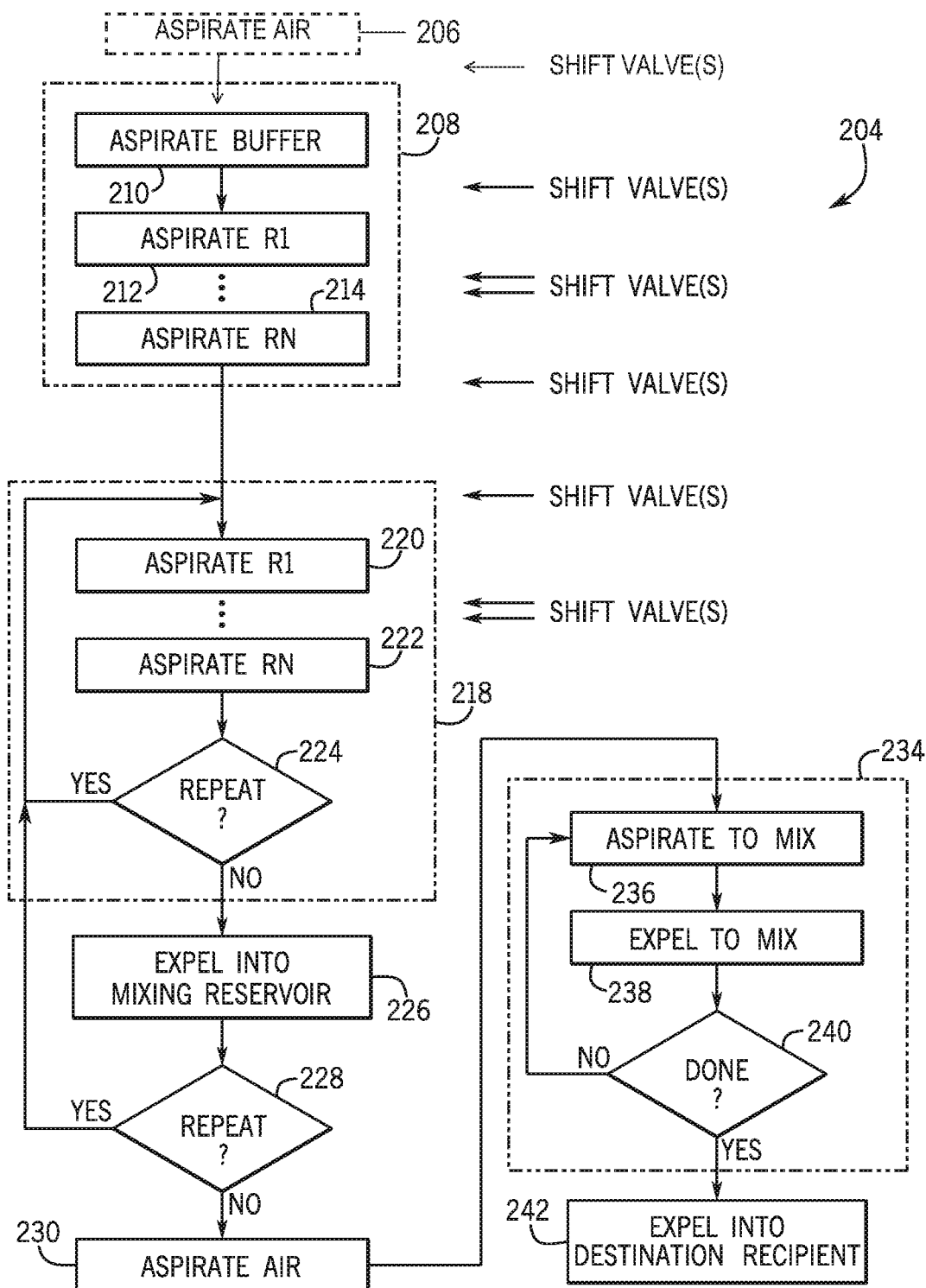
FIG. 12 is a flow chart illustrating a method and example logic for aspirating and mixing reagents and a sample template according to an example.

FIG. 11 is a graphical representation 180 of an example cycle in aspirating and mixing reagents and a sample template according to an example. FIG. 12 is a flow chart illustrating a method and control logic 204 for aspirating and mixing reagents and a sample template according to an example. In FIG. 11, the y-axis 182 represents pressures in psi applied by the pump 38, and the x-axis 184 represents time in seconds. Negative pressures indicate aspiration of one or more of the reagents, while positive pressures indicate ejection. The cycle 180 may be considered to include a "transfer" sequence 186, followed by a "mixing" sequence 196, as discussed below. The method 204 shown in FIG. 12 may correspond to a routing of a mixing protocol 90 that is stored in the memory circuitry 50. The control circuitry 46 of the instrument 12 may access and retrieve the mixing protocol 90 from the memory circuitry 50. The control circuitry 46 may automatically implement the mixing protocol 90 to perform the method 204 onboard the instrument 12 by controlling the operations of the pump 38, the reagent selector valve 66, and the common line selector valve 68, among other components of the instrument 12.

Referring to the flow chart in FIG. 12, the method and control logic 204 may begin with aspirating air, at 206, to remove existing liquid from flow paths through which previous mixtures of reagents may have been routed. For example, any leftover liquid remaining in the flow path 142, which links the reagent selector valve 66 with the destination recipient (e.g., template or mixing reservoir 136), may be aspirated with air (i.e., such that the liquid is replaced with air) so that any new mixture of reagents that is subsequently delivered to the destination recipient via the flow path 142 is not commingled with the leftover liquid.

A transfer sequence may then begin with a priming sequence at 208. The priming sequence is indicated by a series of negative pressure or aspiration events collectively indicated by reference 188 in FIG. 11. In general, the priming sequence draws fluids, such as buffer fluids, the reagents, and other fluids initially into the system. At 210, a buffer may be aspirated. The buffer may comprise a liquid selected so as to be non-reactive or relatively inert with respect to the reagents and may be used as an incompressible working fluid that extends, at least in part, between the pump and the reagents to allow for more precise metering of the reagents into the mixing volume in the following steps, if desired. At 212, a first reagent may then be aspirated in a priming event, followed by aspiration of any number of other reagents through the aspiration of a final reagent at 214. In an example, three reagents are aspirated in the priming sequence, but other examples may include different numbers of reagents aspirated in a priming sequence.

The priming sequence 208 is followed by the remainder of the transfer sequence at 218, during which the reagents to be mixed are aspirated into the system. The transfer sequence is illustrated by the negative pressure events collectively indicated by reference numeral 190 in FIG. 11. The reagents are aspirated in an ordered sequence. For example (in FIG. 12), a first reagent is aspirated at 220, followed by aspiration, one-by-one, of each of the additional reagents in a designated sequence until the final reagent is aspirated as indicated at 222. The amounts of the reagents that are aspirated in each sequence form a set. Three reagents are aspirated in one example, but different numbers of reagents may be aspirated in other examples. The reagents are aspirated into a cache channel (e.g., cache channel 118). As described above, the reagents may be aspirated in relatively small quantities or amounts to create an alternating pattern of the reagents in the cache channel, and thereby promote pre-mixing. At 224, a determination is made whether all sets of the reagents have been aspirated. For example, the system may be controlled to aspirate multiple sets of the reagents, such as five sets. After the first through fourth sets are aspirated, it is determined that not all sets have been aspirated so flow of the method 204 returns to 220 to continue aspirating one or more additional sets. All of the sets may contain all of the reagents, or alternatively at least some of the sets may not include all of the reagents. Moreover, different volumes or quantities of reagents could be aspirated in the various sets. Once all of the sets of the reagents have been aspirated, the method 204 advances to 226. As shown in FIG. 12, and as illustrated by the separate negative (and positive) pressure events of FIG. 11, each successive aspiration (or ejection) of reagents involves controlling one or more of the valves described above, as well as the pump. That is, to aspirate the individual reagents, the reagent selector valve will be shifted to direct negative pressure to the sipper for the corresponding reservoir of the selected reagent. The pump will similarly be commanded to draw the reagent (or air or buffer or template), and to express the aspirated fluids in accordance with the prescribed protocol. This mixing protocol will be predetermined and stored in the memory circuitry described above and carried out in an automated or semi-automated fashion based upon the sequencing operation, also defined in the memory circuitry. These protocols are executed by the processing and control circuitry which, through appropriate interface circuitry commands operation of the valves and pump.

At 226 in FIG. 12, the reagent mixture is ejected or discharged from the cache channel into a mixing reservoir. The ejection into the mixing reservoir is indicated by the positive pressure event 192 in FIG. 11. The mixing reservoir may contain a sample template therein prior to ejecting the reagent mixture. For example, the mixing reservoir optionally may be a template reservoir that is pre-loaded with the sample template, or alternatively may be a different reservoir into which the sample template is transferred. In certain examples, aspiration may be further performed as indicated at reference 228 in FIG. 12. For example, after discharging some of the sets of the aspirated reagents into the mixing reservoir, one or more additional sets of the reagents may be drawn into the cache channel and then subsequently ejected into the mixing reservoir.

Once the aspirations are completed, flow of the method/logic 204 continues to 230 and air may be aspirated into the system. The aspiration of air (or de-priming) is illustrated by the negative pressure event 194 in FIG. 11. The de-priming is performed to remove at least some liquid from the fluid lines, such as the bypass line, cache channel, and nozzle sipper. The air that is introduced may form an air gap that prevents dilution of the reagents and sample template with a buffer fluid within the lines.

Following aspiration and partial pre-mixing in the cache channel by the operations described above, a mixing sequence is performed at 234 by repeatedly moving the reagents and the sample template in the mixing reservoir through a nozzle sipper. In this sequence 234, the combined reagents and template that define a clustering mixture are aspirated at 236 by drawing the clustering mixture through the nozzle sipper into the fluid lines, such as the cache channel. As described above, an air gap may provide a buffer that prevents the clustering mixture from diluting into the buffer fluid in the system. At 238, the aspirated volume of the clustering mixture is ejected back into the mixing reservoir. At 240, a determination is made whether to perform another mixing cycle that includes the aspiration and ejection steps. For example, multiple mixing cycles may be performed to provide a homogenous clustering mixture. In one example, the mixing is repeated three times for a total of four mixing cycles before the mixing is complete. In the graphical illustration of FIG. 11, the cycles are collectively indicated by reference 198. Each mixing cycle involves a relatively short negative pressure event followed by a relatively short positive pressure event. While any desired volume may be displaced in each cycle of the mixing process, in one example, approximately 2 mL (2,000 µL) of the clustering mixture is aspirated from and ejected into the mixing reservoir in each mixing cycle, although other implementations may dispense about 500 µL or 1500 depending on the size of the flow cells that are used. At the end of the mixing process, the mixed clustering mixture may be expelled or delivered to a destination recipient at 242 for proceeding with the sequencing operation. For example, the clustering mixture may be delivered to the flow cell 20 (shown in FIG. 2) to produce clonal populations of DNA molecules on the flow cell that originate from nucleic acids in the sample template.

In an alternative example, the reagents are mixed within the mixing reservoir without the sample template present in the mixing reservoir. Therefore, the reagent mixture may be aspirated and discharged at least once in the mixing reservoir. The sample template may be introduced to the mixed reagents subsequently, such as on the flow cell or within another destination recipient.

ADDITIONAL NOTES

The terms "comprise," "include," "contain," etc., and variations thereof, that are used in the specification and claims herein are intended to be open-ended, including not only the recited elements, but further encompassing any additional elements. Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is also to be understood that the use of "to," e.g., "a valve to switch between two flow paths," may be replaceable with language such as "configured to," e.g., "a valve configured to switch between two flow paths", or the like.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

It is to be understood that the ranges provided herein include the stated range and any value or sub-range within the stated range. For example, a range of from about 10 cP to about 50 cP, should be interpreted to include not only the explicitly recited limits of from about 10 cP to about 50 cP, but also to include individual values, such as about 16 cP, 37.5 cP, 49 cP, etc., and sub-ranges, such as from about 25 cP to about 30 cP, etc. Furthermore, when "about," "approximately," and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A system, comprising:
   reagent reservoirs containing different reagents;
   a mixing reservoir to receive one or more of the reagents;
   multiple sippers including a nozzle sipper and multiple reagent sippers, the reagent sippers respectively extending into the reagent reservoirs such that respective distal tips of the reagent sippers contact the reagents in the reagent reservoirs, and the nozzle sipper extending into the mixing reservoir;
   a cache channel positioned upstream of the mixing reservoir and extending between a pump end and a reservoir end, the pump end of the cache channel operatively connected to a pump;
   a reagent selector valve fluidly connected to the reservoir end of the cache channel and fluidly connected to each of the sippers through corresponding fluid channels;
   one of:
      an inlet of the mixing reservoir for pre-loading of a sample template; or
      a template reservoir containing a sample template and fluidly connected to the reagent selector valve through an other sipper and corresponding fluid channel;
   a control circuitry operatively connected to the pump and the reagent selector valve, the control circuitry implementing a mixing protocol by controlling the pump and the reagent selector valve to automatically aspirate the reagents through the corresponding reagent sippers into the cache channel at designated amounts of the corresponding reagents based on the mixing protocol to pre-mix the reagents, the control circuitry subsequently i) controlling the pump and the reagent selector valve to discharge the reagents from the cache channel through the nozzle sipper into the mixing reservoir and mix the reagents with the sample template pre-loaded within the mixing reservoir to form a reagent mixture or ii) controlling the pump and the reagent selector valve to discharge the reagents from the cache channel through the nozzle sipper into the mixing reservoir and to discharge the sample template from the template reservoir directly to the mixing reservoir to form a reagent mixture.

2. The system of claim 1, wherein the control circuitry controls the pump to mix the reagents within the mixing reservoir by aspirating a volume of the reagent mixture into the nozzle sipper and subsequently discharging the volume of the reagent mixture from the nozzle sipper back into the mixing reservoir.

3. The system of claim 2, wherein the control circuitry controls the pump and the reagent selector valve to aspirate and subsequently discharge the reagent mixture within the mixing reservoir multiple times to mix the reagents.

4. The system of claim 2, wherein the nozzle sipper contains a buffer fluid therein, the control circuitry controlling the pump to introduce air into the nozzle sipper prior to aspirating the reagent mixture into the nozzle sipper to define an air gap between the buffer fluid and the reagent mixture that is aspirated into the nozzle sipper to avoid mixing the buffer fluid and the reagent mixture.

5. The system of claim 1, wherein an inner diameter of the nozzle sipper is smaller than respective inner diameters of the reagent sippers.

6. The system of claim 1, wherein the control circuitry controls the pump and the reagent selector valve to aspirate the reagents into the cache channel one at a time in an ordered sequence and to repeat the ordered sequence at least once before the reagents in the cache channel are discharged into the mixing reservoir.

7. The system of claim 1, wherein the control circuitry controls the pump and the reagent selector valve to aspirate a first volume of the reagents into the cache channel and to subsequently discharge a second, smaller volume of the reagents from the cache channel into the mixing reservoir such that a residual volume of the reagents defining an upstream buffer zone remains in the cache channel after discharging the reagents into the mixing reservoir.

* * * * *